United States Patent [19]
Coutts

[11] Patent Number: 5,514,137
[45] Date of Patent: May 7, 1996

[54] FIXATION OF ORTHOPEDIC DEVICES

[76] Inventor: Richard D. Coutts, 4210 Ridgeway, San Diego, Calif. 92116

[21] Appl. No.: 163,908

[22] Filed: Dec. 6, 1993

[51] Int. Cl.⁶ ..................................................... A61F 5/04
[52] U.S. Cl. ............................... 606/62; 606/92; 606/93; 606/77
[58] Field of Search ................................ 606/92–95, 62, 606/64, 77, 76

[56] References Cited

U.S. PATENT DOCUMENTS

| | | | |
|---|---|---|---|
| 3,030,951 | 4/1962 | Mandarino | 606/93 X |
| 3,805,776 | 4/1974 | Thiele | 606/93 X |
| 4,274,163 | 6/1981 | Malcom et al. | 606/94 |
| 4,653,487 | 3/1987 | Maale | 606/94 X |
| 4,653,489 | 3/1987 | Tronzo | 606/93 X |
| 4,751,921 | 6/1988 | Park | 606/93 |
| 4,756,307 | 7/1988 | Crowninshield | 606/77 |
| 4,760,844 | 8/1988 | Kyle . | |
| 4,880,610 | 11/1989 | Constantz . | |
| 5,129,905 | 7/1992 | Constantz | 606/76 |
| 5,192,282 | 3/1993 | Draenert | 606/92 X |
| 5,192,283 | 3/1993 | Ling et al. | 606/93 |
| 5,268,000 | 12/1993 | Ottieri et al. | 606/62 |

OTHER PUBLICATIONS

Shifflett, et al., "Preventing Complications of Interlocked Nailing in Intramedullary Fixation of the Femur", *Complications in Orthopedics*, Sep./Oct., 1987, pp. 116–122.
Andriano, et al., "Biocompatibility and Mechanical Properties of a Totally . . . ", *Journal of Applied Biomaterials*, 3:197–206 (1992).
Baker, et al., "An In Vivo Evaluation of Artificial Bone Constructs", *Orthopedic Research Society*, 38th Annual Meeting, Feb., 1992.
Bankston, et al., "The Biomechanical Evaluation of Intramedullary Nail in Distal Femoral Shaft Fractures", *Orthopedic Research Society*, 1986 Annual Meeting.
Browner, "The Grosse–Kempf Locking Nail", *Contemporary Orthopaedics*, 8:3:17–25, Mar. 1984.
Bucholz, et al., "Fatigue Fracture of the Interlocking Nail in the Treatment . . . ", *Journ. of Bone and Joint Surgery*, 69A:9:1391, Dec. 1987.
Constantz, et al., "Evaluation of Bioactive Cements Using a Rabbit Femoral Canal Model", *Orthopaedic Research Society*, 38th Annual Mtg., Feb. 1992.
Coutts, et al., "The Evaluation of a Bioresorbable Cement for the Temporary . . . ", *Orthopedic Research Society*, 38th Annual Meeting, Feb. 1992.
Damien, et al. "Bone Graft and Bone Graft Substitutes: A Review . . . " *Journal of Applied Biomaterials*, 2:187–208 (1991).
Enis, et al., "Effects of Methylmethacrylate in Osteosynthesis", *Clin. Orthop.*, 105:283–294, Nov. 1974.
Gerhart, et al. "In Vitro Characterization and Biomechanical Optimization . . . ", *Journ. of Biomed. Mat. Res.*, 22:1071–1082 (1988).
Giachino, et al., "Irradiation of the Surgeon During Pinning of Femoral Fractures", *Journ. of Bone and Joint Surgery*, 62B:2:227–229, May 1980.
Hollinger, et al., "Biodegradable Bone Repair Materials", *Clin. Orthop.*, 207:290–305 (1986).
Johnson, et al., "Comminuted Femoral–Shaft Fractures: Treatment by Roller Traction . . . ", *Journ. of Bone and Joint Surg.*, 66A:8:1222–1235 Oct. 1984.
Johnson, et al., "Biomechanical Performance of Locked Intramedullary Nail Systems . . . ", *Clin. Orthop.*, 206:151–161, May 1986.

(List continued on next page.)

Primary Examiner—Stephen C. Pellegrino
Assistant Examiner—Michael Peffley
Attorney, Agent, or Firm—Knobbe, Martens, Olson & Bear

[57] ABSTRACT

The present invention relates to methods to provide superior fixation of orthopedic devices within bones, through use of a resorbable cement material. As well, methods to provide temporary fixation of orthopedic devices within bones until the natural bone tissue may ingrow with the device are also disclosed. The methods are broadly applicable to repair of fractures or other divisive or compressive maladies in bones, augmentation of the osteopenic skeleton, and attachment of prostheses.

36 Claims, 19 Drawing Sheets

OTHER PUBLICATIONS

Jones, et al., "Bulk Hydroxyapatite: Evaluation of Its Use as a Bone Graft Substitute", *Society for Biomaterials* 17th Annual Meeting, May 1991.

Kempf, et al. "Closed Locked Intramedullary Nailing", *Journ. of Bone and Joint Surg.*, 67A:5:709–720, Jun. 1985.

Kessler, et al., "The Effects of Reaming and Intramedullary Nailing on Fracture Healing", *Clin. Orthop.*, 212:18–25, Nov., 1986.

Kyle, et al., "Biomechanical Characteristics of Interlocking Femoral Nails . . . ", *Clin. Orthop.*, 267:169–173, Jun. 1991.

Levin, et al., "Radiation Exposure to the Surgeon During Closed Interlocking Intramedullary Nailing" *Journ. of Bone and Joint Surg.*, 69A:5:761–766, Jun. 1987.

Miller, et al., "Radiation Exposure and Associated Risks to Operating–Room . . . ", *Journ. of Bone and Joint Surg.*, 65A:1:1–4. Jan. 1983.

Oonishi, et al., "Fully Bioactive Bone Cement Using Tetra–Calciumphosphate and Collagen", *Society for Biomaterials*, 17th Annual Mtg., May 1991.

Oonishi, et al., "Interface Bioactive Bone Cement as Functional Gradient Materials", *Dept. of Orthop. Surg.*

Rao, et al., "Distal Screw Targeting of Interlocking Nails", *Clin. Orthop.*, 238:245–248 Jan. 1989.

Shors, et al., "The Material and In Vivo Properties of a Biodegradable Bone Graft Substitute", *Society for Biomaterials*, 17 Ann. Mtg., 1991.

Tarr, et al., "The Mechanics and Biology of Intramedullary Fracture Fixation", *Clin. Orthop.*, 212:10–17, Nov. 1986.

Thoresen, et al., "Interlocking Intramedullary Nailing in Femoral Shaft Fractures", *Journ. of Bone and Joint Surg.*, 67A:9:1313–1320, Dec. 1985.

Weber, et al., "A Comparison of the Mechanical Properties of Simplex Zimmer . . . ", *Biomat. Med. Dev. Art. Ort.*, 11:(1):3–12 (1983).

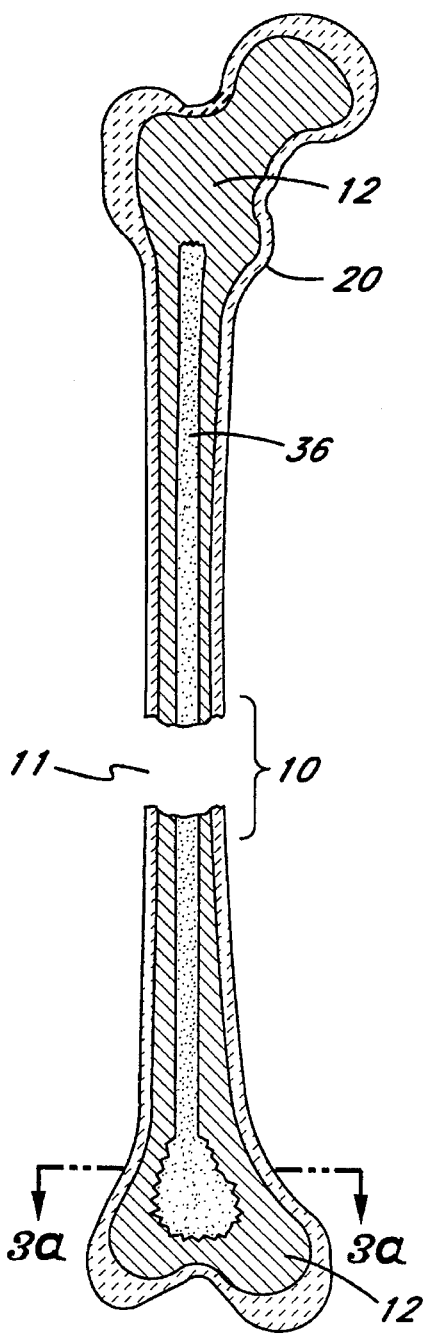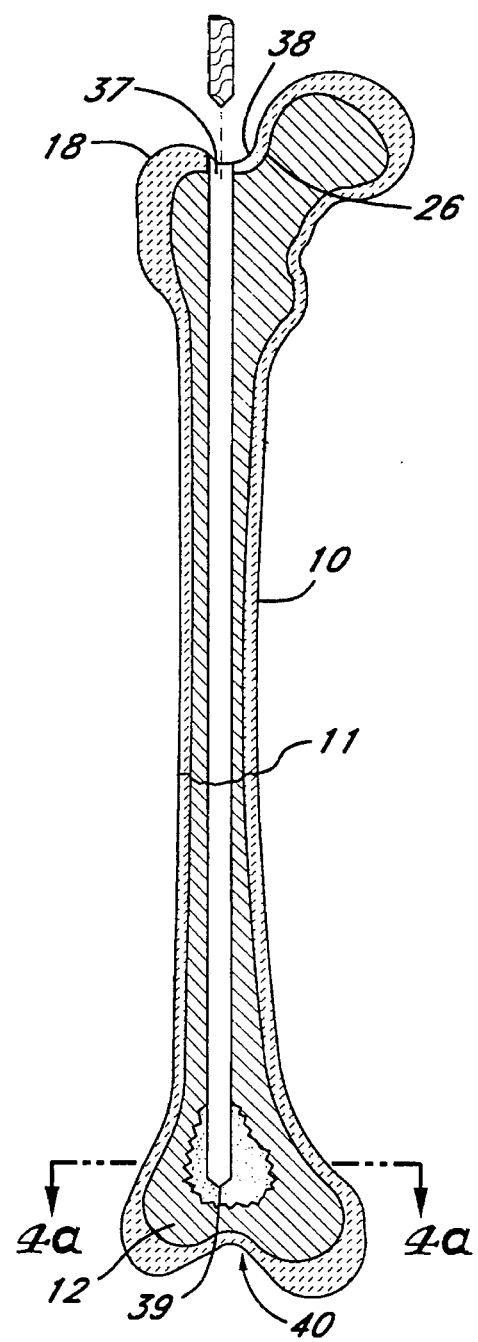
Fig. 3
Fig. 4
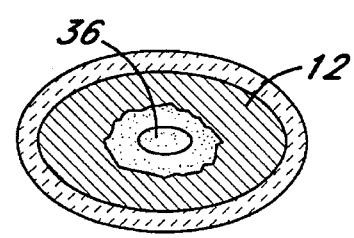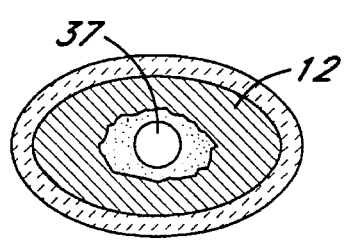
Fig. 3a
Fig. 4a

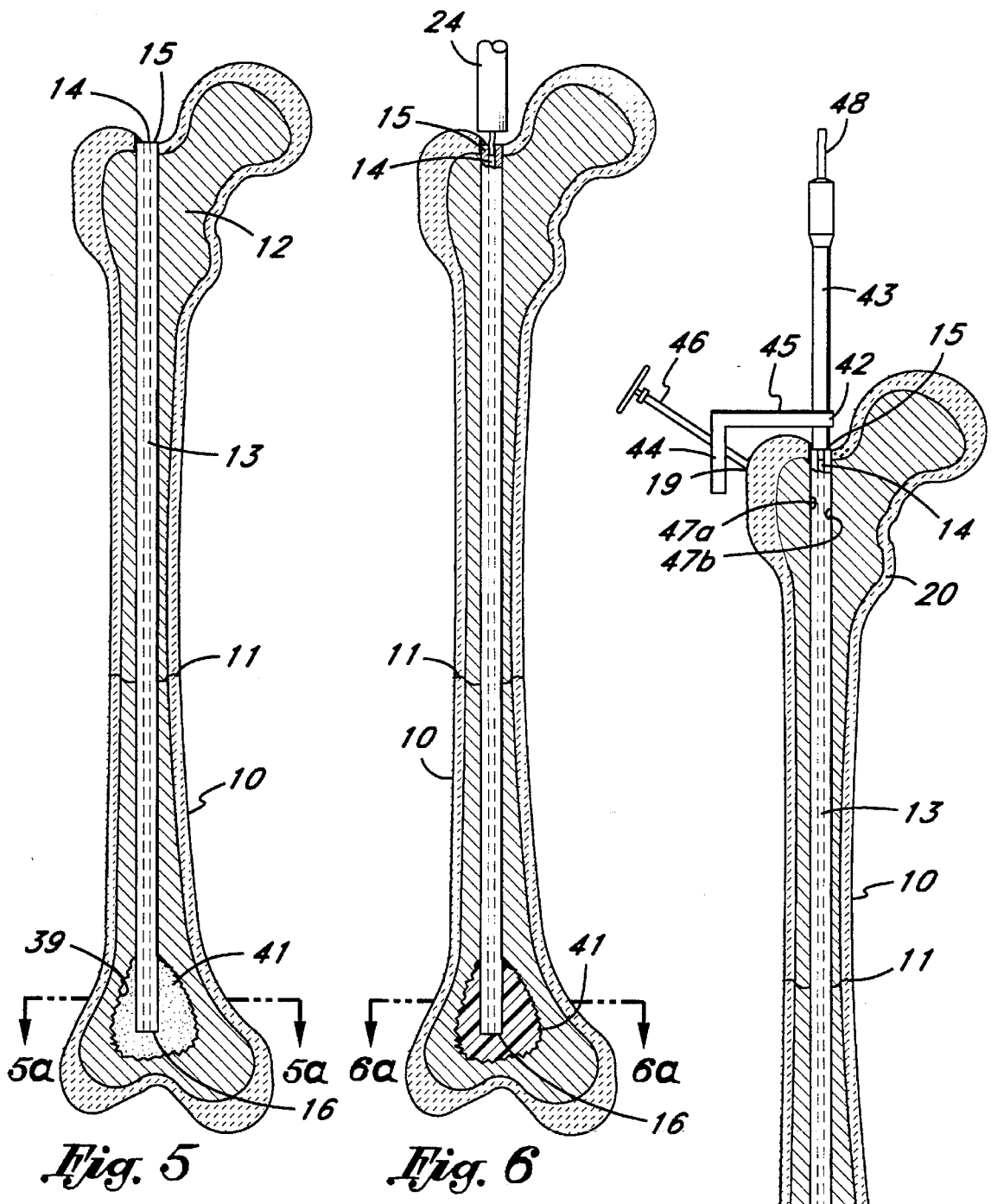

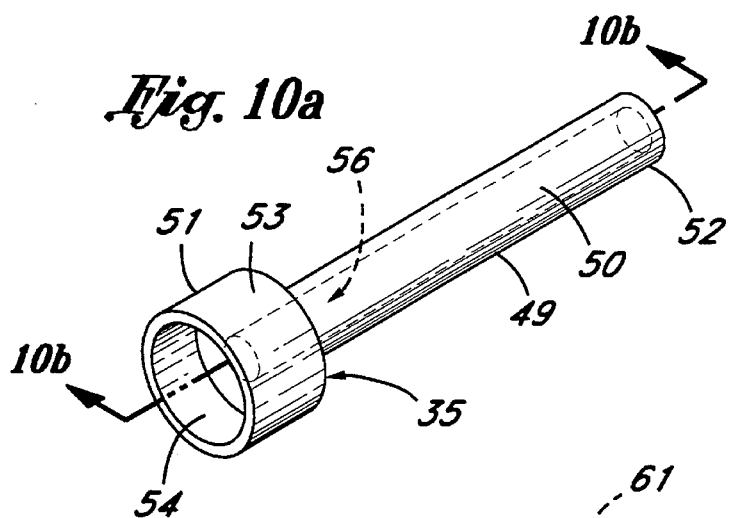
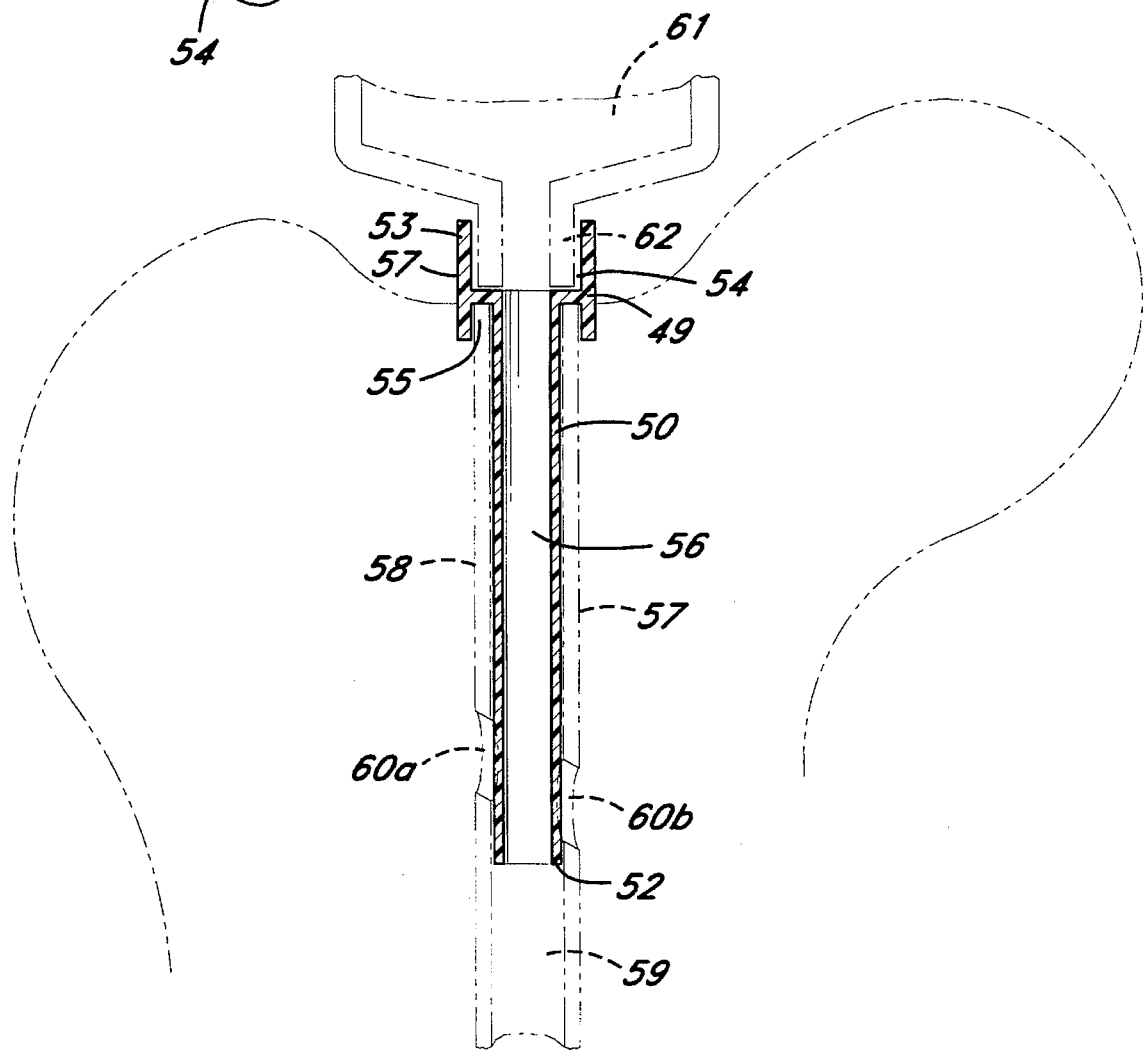

- LOAD CELL
- CROSSHEAD
- INTRAMEDULLARY ROD
- BOVINE FEMUR
- MOUNTING JIG

- LOAD CELL
- CROSSHEAD
- STEEL CABLE
- ROD CLAMPS
- TORSION DISC
- INTRAMEDULLARY ROD

FIXATION OF ORTHOPEDIC DEVICES

BACKGROUND OF THE INVENTION

1. Field of the Invention

The present invention relates to a method to provide temporary fixation of orthopedic devices, in particular intramedullary rods, other fracture fixation devices, and prostheses, that provides a substitute for conventional methods for fixation at both the distal and proximal end of the device.

2. Background of the Art

Interlocking intramedullary rod nailing requires fixation of the distal and proximal portions of an intramedullary rod to a bone. Typically, the canal of the bone is drilled from a proximal to a distal end of the bone and an intramedullary rod is inserted. Transfixion screws are then placed through holes in the intramedullary rod. To insert the screws, holes are drilled through the bone at an angle of between about 30 and 90 degrees to the rod, and screws are inserted through the holes to lock the intramedullary rod in place.

As will be appreciated, since the rod is buried in the intramedullary space of the bone, aiming devices or jigs are necessary in order to accurately drill the holes through the bone to match up with the holes of the intramedullary rod. This technique is relatively straightforward near the proximal end of the intramedullary rod (near its point of insertion). In this region, a relatively short-armed aiming device can be attached to the intramedullary rod for reference. Thereafter, a drill can be passed through the bone and a proximal hole.

However, in the distal region, accuracy is affected due to the distance between the reference point (the proximal end of the rod) and the point where the holes must be drilled. Freehand drilling while watching a fluoroscopic image intensifier to accomplish distal targeting is one solution to this problem. However, this technique is difficult to use and adds the additional risk of exposing the patient and surgical team to radiation. E.g., Muller et al. *J. Bone & Joint Surgery* (hereinafter abbreviated "JBJS") 65A:1–4 (1983); Levin et al. JBJS 62B:227–229 (1987); Rao et al. *Clin. Ortho.* Rel. Res., 238:245–248 (1989); Gachino et al. *JBJS*, 69A:761–766 (1987).

The Brooker-Wills rod attempts to circumvent the problem presented by the difficulties encountered in fixing the distal end of intramedullary rods. This rod functions through use of an internal mechanism in the rod that allows placement and deployment of expandable fins from the distal end of the rod. While easier to use, the rod is fixed less rigidly, rendering the intramedullary rod less effective against axial and torsional loads. E.g., Johnson et al. *Clin. Ortho. Rel. Res.* 206:151 (1986); Kyle et al. *Clin. Ortho. Rel. Res.* 267:169–173 (1991); Bankston et al. [CITE] (1992).

Despite these problems, all of the interlocking nail techniques share in common an enhanced ability to control the axial and torsional forces that are often encountered where such interlocking is not used. Shortening and angulation of the fractured bone are prevented, resulting in a superior ability to restore the normal anatomy of the patient. Further, because of its success, the use of interlocking screws with intramedullary rods has gained favor in the treatment of comminuted and unstable fractures as well as other fractures located proximal or distal to the mid-diaphysis where good nail fixation has been difficult to achieve with conventional rods.

The clinical results of interlocking intramedullary rods with screws have been impressive. E.g., Johnson et al. *JBJS* 66A: 1222 (1984); Kempf et al. *JBJS* 67A: 709 (1985); Browner et al. *Contemp. Ortho.* 8:17–25 (1984); Thoresen et al. *JBJS* 67A:1313 (1985). In particular, comminuted fractures of the distal and proximal one-third of the femur and tibia that previously could not be managed by closed intramedullary nails are now candidates for interlocking rod fixation. The rapid functional recovery and lower morbidity associated with this technology will likely further the indications for, and use of, this technique.

Complications with interlocking nails have been noted, however. These include difficulty of screw placement, as discussed above, and bending, fracturing, and/or loosening of the nail or other implant. Shifflett et al. Complications in Ortho. 116:$_{13}$ (1987); Bucholtz et al. JBJS 69A:1391 (1987). There is also the concern of increased operative time and radiation exposure with the interlocking process. These particular complications are specifically related to the design and use of the interlocking rod.

Another avenue that has been explored is the permanent fixation of intramedullary rods as well as protheses in the intramedullary space within bones through the use of certain synthetic polymer cements. In particular, the use of methyl acrylate, polymethacrylate, or polymethylmethacrylate (PMMA) styrene copolymers has been suggested. E.g., U.S. Pat. No. 4,065,817 to Branemark, et al.; U.S. Pat. No. 4,494,535 to Haig; and U.S. Pat. No. 4,635,489 to Tronzo.

Of the patents mentioned above, U.S. Pat. No. 4,494,535 to Haig and U.S. Pat. No. 4,635,489 to Tronzo both disclose the permanent fixation of a hip nail with an acrylic cement. Also, a system has been proposed that is useful for prevention of fractures and augmentation of the osteopenic skeleton. The system involves the insertion of an intramedullary rod in the femur and the injection of acrylate polymer cement to permanently fix the rod within the femur. See U.S. Pat. No. 4,653,487. However, this latter system is designed specifically for preventing an intramedullary rod from telescoping through a weakened and diseased bone; i.e., augmentation, not for the repair of a fracture or for the fixation of a prosthesis anchor.

Synthetic polymer cements cure through exothermic reactions, thereby producing elevated temperatures in the surrounding tissues while undergoing polymerization. For example, PMMA cements typically react and release heat at up to 50°–70° C. This may lead to tissue destruction around the area where the cement is applied causing occlusion of nutrient arteries in the bone. Similarly, certain of the cements are toxic to surrounding tissues upon introduction and may also lead to cell death. If no cell death occurs, the cements may lead to local inflammation. Once polymerized, the cements remain in the bone permanently.

To combat these problems, several partially or completely resorbable bone cements have been proposed. E.g., U.S. Pat. No. 4,296,209 to Tomic (partially resorbable effervescent composition based on polymethylmethacrylate, calcium carbonate, and disodium hydrophosphate); U.S. Pat. No. 5,019,379 to Domb et al. (resorbable unsaturated polyanhydride compositions); U.S. Pat. Nos. 4,365,357 and 4,373,217 to Draenert (partially resorbable mesh for allowing ingrowth into nonresorbable PMMA-type cements and partially resorbable PMMA-type cements with tricalcium phosphate, respectively); and U.S. Pat. Nos. 4,880,610, 5,047,031, 5,053,212, and 5,129,905 to Constantz (resorbable hydroxyapatite compositions).

A need therefore remains in the orthopedic fixation art for a method to provide fixation of devices within bones that alleviate the problems of difficulty of interlocking of intramedullary structures, bone ingrowth incompatibilities with conventional cements, and attainment of the necessary strength and rigidity of the implant, and ultimate removal of the cement by natural biologic processes.

SUMMARY OF THE INVENTION

We have surprisingly discovered that completely or partially resorbable cements fix an implant to bone in a manner that is comparable in strength to methacrylate cements. Accordingly, the present invention relates to the discovery of a method for effectively using bone cement, preferably completely or substantially resorbable bone cement, to provide a unique fixation of an implant within a bone. Moreover, in the preferred embodiment, the fixation is only temporary until resorption and/or osteogenesis has occurred. The novel cement injection techniques of the present invention provide a secure, complete cementing of an end of the device or implant that is at least equivalent to conventional cementing.

In accordance with a first aspect of the present invention, a method to repair a fractured bone is provided. The method preferably comprises the steps of reaming a canal in the bone to form a longitudinal channel extending from a first end to a second end of the bone, the channel having a proximal opening, a proximal portion, and a distal end; injecting an effective amount of a resorbable cement material into the distal end of the channel; inserting into the channel an intramedullary rod, having a proximal end and a distal end, such that the distal end of the rod contacts the cement; and allowing the cement to cure thereby anchoring the rod to the bone, such that a bond strength between the rod and the bone is sufficient to withstand physiological loads during a healing period of the fracture until the bone can withstand normal physiological loads without augmentation.

In a preferred embodiment, a cement introducer device is used in the injecting step. In another preferred embodiment, the rod is hollow and the inserting step precedes the injecting step, wherein the cement is injected through the rod. In another preferred embodiment, the rod may further comprise interlocking aiming holes near the proximal end and the method further comprises the use of a bypass nozzle in the injecting step. In the alternative, the rod may further comprise a plurality of grooves on the distal end to aid in providing greater contact between the cement and the rod. The resorbable cement material is preferably a calcium compound or salt, such as calcium sulfate, calcium phosphate, and/or calcium carbonate derivatives (together, and generally, calcium based materials will be referred to herein as "calcium derivatives"). Also, preferably, the cement includes hydroxyapatite, orthophosphoric acid, and one or more other calcium derivatives, such as calcium carbonate and calcium hydroxide formed into a semi-liquid paste with an alkaline solution of sodium hydroxide and water. In another preferred embodiment, the resorbable cement material is a composition comprising polypropylene fumarate, preferably, comprising a calcium salt filler, N-vinyl-2-pyrrolidone, and a peroxide or free radical initiator. In another preferred embodiment, the resorbable cement material comprises a mixture of calcium phosphates, preferably, comprising tetracalcium phosphate and dicalcium phosphate. The resorbable cement material may additionally contain an active agent, selected from the group consisting of antibiotics, bone growth promoters, vasoactive agents, and other drugs. The method preferably additionally comprises, after the injecting and inserting steps, drilling a hole in the proximal end of the bone through the rod and inserting an interlocking device therethrough. The method also preferably comprises, after the injecting and inserting steps, the cement undergoing resorption with or without osteogenic growth occurring around the distal end of the rod. The bone is preferably selected from the group consisting of a femur, a tibia, a humerus, a radius, and an ulna.

In accordance with another aspect of the present invention, there is provided a method to fix orthopedic implants in a bone, comprising preparing the bone for implant insertion; reaming a canal in the prepared bone, such that at least a portion of the cancellous tissue of the bone is exposed, the hole sized for the implant; applying an effective amount of a resorbable cement, such that the cement provides fixation surfaces between at least a portion of the implant and at least a portion of the cancellous tissue of the bone and the cement; and allowing the cement to cure within the bone, such that a complete filling or bond is formed between at least a portion of the implant and at least a portion of the cancellous tissue of the bone through the cement such that the fixation is of sufficient strength to withstand physiological loads.

In the method, the implant preferably has a proximal end and a distal end, and a bore extending therebetween, and the inserting step precedes the applying step, wherein, in the applying step, the resorbable cement material is injected through the bore. In the alternative, the applying step may comprise deploying the resorbable cement material onto the exposed cancellous tissue and onto the implant. Preferably, the resorbable cement material is a calcium derivative. Moreover, preferably the calcium derivative is generally composed of hydroxyapatite, orthophosphoric acid, calcium carbonate, and calcium hydroxide formed into a semi-liquid paste with an alkaline solution of sodium hydroxide and water. In another preferred embodiment, the resorbable cement material is a composition comprising polypropylene fumarate, preferably, comprising a calcium salt filler, N-vinyl-2-pyrrolidone, and a peroxide or free radical initiator. In another preferred embodiment, the resorbable cement material comprises a mixture of calcium phosphates, preferably, comprising tetracalcium phosphate and dicalcium phosphate. The resorbable cement material may additionally contain an active agent, selected from the group consisting of antibiotics, bone growth promoters, vasoactive agents, and other drugs. The implant may have a substantially tubular structure. For example, the implant is preferably an intramedullary rod. Or, the implant may have a substantially conical structure. In the alternative, the implant may further comprise a plurality of grooves on the distal end to aid in providing greater contact between the cement and the implant. Alternatively, it may be a threaded (screw) device, or a solid rod.

A cement introducer device can be used in the applying step of the method. Alternatively, where an intramedullary rod is used, it preferably has a proximal end and a distal end and a bore extending therebetween and the applying step further comprises injecting cement through said bore. The rod may further comprise interlocking aiming holes near the proximal end and the method preferably further comprises the use of a bypass nozzle in the applying step.

In another embodiment of the present invention, there is provided a method to repair a comminuted fracture in a bone, comprising providing a bone having a comminuted fracture comprising one or more fragments each fragment being separated by a space from a main portion of the bone; applying a resorbable cement to the space; and pushing each fragment into a proper alignment with the main portion of the bone thereby substantially eliminating said space and forming a bond between the cement, the fragments, and the main portion of said bone. In a preferred embodiment the method further comprises the step of, after the pushing step, holding the fragments and the main portion of the bone together. In this embodiment, the holding step preferably further comprises fitting plates around the fracture and screwing the plates to the bone. Alternately or in addition, the method can further comprise wrapping the fracture with circlage in the holding step. And the entire repair could be reinforced with an intramedullary rod, inserted prior to cement curing.

In another aspect of the present invention, there is provided a cement introducer device, comprising an elongate flexible shaft having a proximal end and a distal end and a lumen extending therebetween; a connector on the proximal end for attaching a feed container containing a resorbable cement; and a feed container attached to said connector containing resorbable cement, said feed container having means for pushing said cement from said container through said lumen and out the distal end of said shaft. The feed container is preferably a syringe. In this embodiment, the connector and the syringe preferably comprise locking type fittings and the syringe is attached to the connector through the locking-type fittings. Preferably, the shaft of the introducer device is sized to fit within an intramedullary channel in a bone and extend from one end of a bone to another. Following introduction of the cement, the hollow flexible tube may serve as a guide for the introduction of a permanent intramedullary fixation device, after which the flexible tube is withdrawn having served the function of maintaining fracture reduction and alignment during the rod insertion process.

In accordance with another aspect of the present invention, there is provided a bypass nozzle, comprising an elongate shaft having a proximal end and a distal end and a lumen extending therebetween, the distal end sized to fit inside a proximal opening on the proximal end of a hollow intramedullary device; and a connector on the proximal end constructed to receive and engage a feed container for introducing resorbable cement through the lumen. In a preferred embodiment, the intramedullary device further comprises side ports for interlocking the device to a bone, the side ports being located distally from the proximal end, and the shaft of the nozzle is long enough to extend beyond the ports when inserted in the proximal opening of the intramedullary device.

BRIEF DESCRIPTION OF THE DRAWINGS AND FIGURES

FIG. 1. is a cross-sectional view of a femur with a fracture in the mid diaphysis after repair in accordance with a preferred method of the present invention.

FIG. 2. is a cross-sectional view of a femur with a fracture in the neck section after repair in accordance with a preferred method of the present invention.

FIG. 3. is a cross-sectional view of a femur with a fracture in the mid diaphysis about to undergo repair in accordance with a preferred method of the present invention.

FIG. 3a. is a top elevational cross-sectional view of the femur taken along line 3a—3a in FIG. 3.

FIG. 4. is a cross-sectional view of a femur with a fracture in the mid diaphysis undergoing repair in accordance with a preferred method of the present invention, particularly showing preparation of a channel within the femur for insertion of an intramedullary rod.

FIG. 4a. is a top elevational cross-sectional view of the femur taken along line 4a—4a in FIG. 4.

FIG. 5. is a cross-sectional view of a femur with a fracture in the mid diaphysis undergoing repair in accordance with a preferred method of the present invention, particularly showing the insertion of an intramedullary rod.

FIG. 5a. is a top elevational cross-sectional view of the femur taken along line 5a—5a in FIG. 5.

FIG. 6. is a cross-sectional view of a femur with a fracture in the mid diaphysis undergoing repair in accordance with a preferred method of the present invention, particularly showing the injection of the resorbable cement.

FIG. 6a. is a top elevational cross-sectional view of the femur taken along line 6a—6a in FIG. 6.

FIG. 7. is a cross-sectional view of a femur with a fracture in the mid diaphysis undergoing repair in accordance with a preferred method of the present invention, particularly showing the step of interlocking of the proximal end.

FIG. 8. is a perspective view of a design of the distal end of an implant in accordance with the present invention.

FIG. 9. is a perspective view of a design of the distal end of an implant in accordance with the present invention, particularly showing grooves on the external wall to enhance bond strength.

FIG. 10a and 10b. is a series of diagrams showing a bypass nozzle of the present invention that is designed to allow cement to be injected through an intramedullary device without being communicated through the interlocking side ports. In FIG. 10a, a front perspective view is provided. In FIG. 10b, a cross sectional view taken along line 10b—10b in FIG. 10a is shown inserted in an intramedullary rod and engaged to an injector device.

FIG. 11. is a cross sectional view of a cement introducer device.

FIG. 12. is a top perspective view of the cement introducer device attached to an injector device.

FIG. 13a and 13b. is a series of drawings showing the use of the cement introducer device.

FIG. 14a–b and 14c, is a series of drawings showing the repair of a comminuted fracture in accordance with the present invention. In FIG. 14a, an interarticular comminuted fracture is shown with a series of fragments. In FIG. 14b, cement is shown being injected into the fractures between the fragments. In FIG. 14c, the fracture is shown after plating and screwing.

FIG. 15. shows a schematic of the compressive testing device.

FIG. 16. shows a schematic of a torsional testing device.

FIG. 17. is a graph showing the relative deformation in millimeters under a load in Newtons of rods bound to bones with polymethylmethacrylate versus a resorbable cement after ten cycles in the compressive testing (FIG. 13).

FIG. 18. is a bar graph showing the compressive stiffness in Newtons per millimeter for rods bound to bone with a resorbable cement versus polymethylmethacrylate.

FIG. 19. is a graph showing the structural properties in torsion as derived from torque in Newton meters versus rotation in degrees of rods bound to bone with polymethylmethacrylate versus a resorbable cement.

FIG. 20. is a graph showing the structural properties in torsion as derived from torque in Newton meters versus rotation in degrees of rods bound to bone with a resorbable cement.

FIG. 21. is a graph showing the averaged structural properties in torsion as derived from torque in Newton meters versus rotation in degrees of rods bound to bone with polymethylmethacrylate versus a resorbable cement.

FIG. 22. is a graph showing the structural properties in torsion as derived from torque in Newton meters versus rotation in degrees of rods bound to bone with polymethylmethacrylate.

FIG. 23a and 23b. is two bar graphs showing torque at failure (FIG. 23a) and rotation at failure (FIG. 23b) for rods bound to bone with polymethylmethacrylate versus a resorbable cement.

FIG. 24a, 24b, 24c and 24d is four bar graphs showing torque at failure (FIG. 24a), rotation at failure (FIG. 24b), compressive stiffness (FIG. 24c), and torsional stiffness (FIG. 24d) for rods bound to bone with polymethylmethacrylate versus a resorbable cement, particularly comparing the effects of injection of the resorbable cement versus hand packing of the resorbable cement.

FIG. 25. is a schematic diagram of the proposed in vivo testing protocol of inducing a fracture in an animal femur and repairing it through the method of the present invention.

FIG. 26. is a schematic diagram of a method to determine torsional strength in the proximal end of the femur in connection with the in vivo testing.

FIG. 27. is a schematic diagram showing the protocol for histological sampling of bone sections.

FIG. 28. is a graph showing the structural properties in torsion as derived from torque in Newton meters versus rotation in degrees of rods bound to bone with a polypropylene fumarate cement, polymethylmethacrylate, and interlocking screws.

DETAILED DESCRIPTION OF THE PREFERRED EMBODIMENTS

Figures 1, 2:
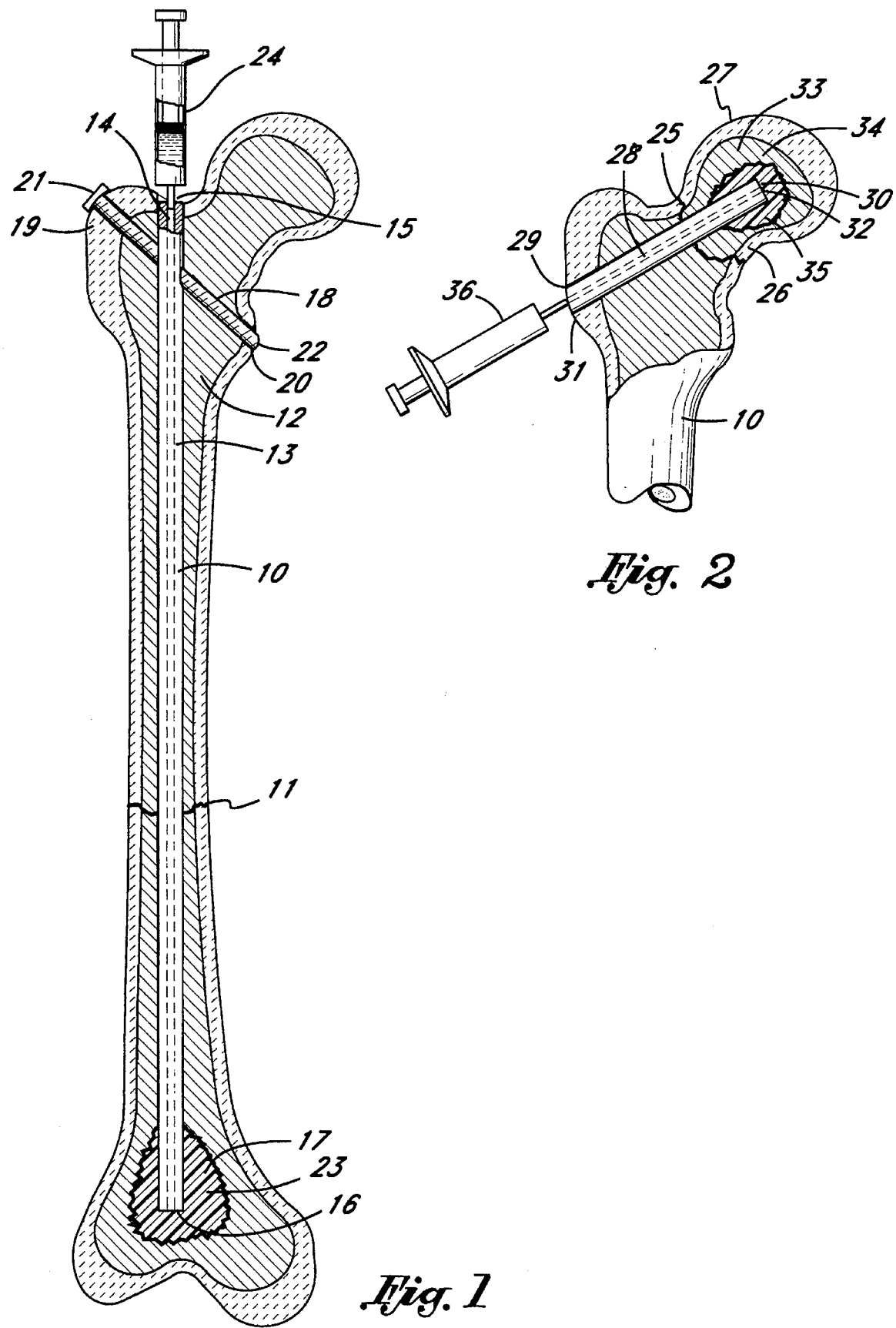
Figure 8:
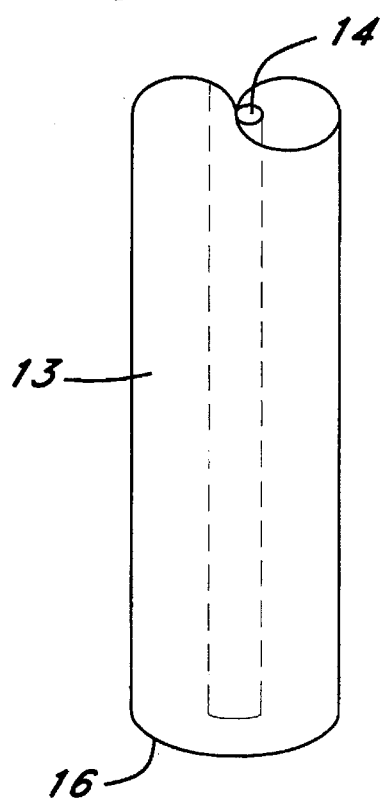

I. Temporary Fixation of a Device Within a Bone to Enable Ingrowth Fixation

A. Resorbable Cements

As will be appreciated, there have been a number of resorbable cement materials proposed for use in a variety of orthopedic and dental applications. Many such resorbable cements contemplate the use of compositions that are related to hydroxyapatite, which is a natural component of bone. The speculated advantages posited for the resorbable cements is that they will be capable of taking part in the natural bone resorption and deposition processes.

As will be appreciated, bones are generally made up of an outer generally solid layer, the cortical layer, that is composed of collagen fibers and the so-called ground substance (primarily hydroxyapatites of the general structure $[Ca^{++}_{10-x}(H_3O^+)_{2x}\bullet(PO_4)_6(OH^-)_2]$ in crystalline form), that is covered by the periosteum tissue, and an inner layer of cancellous tissue (spongy bone) also composed of the above materials. Also, several different cell types are present in the bone, as will be discussed below, as well as an arterial, venous, and neural system. Moreover, in the long bones, for example, in the arms and legs, there is a hollow cavity (intramedullary cavity) in the center of the bone that is filled with marrow and, in some cases, certain quantities of cancellous tissue.

In the process of bone formation, cells called osteoblasts secrete collagen which is rapidly bonded to form collagen fibers and the resultant tissue becomes osteoid, in which calcium salts will precipitate therein. Also, as the osteoblasts secrete collagen, they become entrapped in the osteoid tissue and become osteocytes, thereby ceasing bone production. Within a few days of formation of the osteoid tissue, calcium salts (i.e., $CaHPO_4$, $Ca_3(PO_4)_2$) precipitate on the surface of the osteoid tissue, eventually forming the complete hydroxyapatite crystals through substitution and addition of atoms.

A competing process also occurs within the bone wherein bone is constantly undergoing resorption. A cell called an osteoclast is responsible for such resorption. The osteoclasts are derived from mesenchymal stem cells that are present in the marrow (the center of the bone) or in the fibrous tissue of the periosteum (the outer layer of the bone). The osteoclasts appear to secrete a variety of proteolytic enzymes and several acids, including citric and lactic acid. The enzymes presumably digest the organic matrix of the bone, while the acids appear to dissolve the salts. The osteoclasts, in this manner, essentially eat holes through the bone.

Thus, there is a continual cycle in the bone of osteoclast formation from the mesenchymal stem cells and their development during which they dissolve the bone matrix, and stem cells also forming osteoblasts, the osteoblasts acting to form the bone matrix, and the entrapment of the osteoblasts within the bone matrix to form the osteocytes (which ceases the production of bone by the osteoblasts which become entrapped osteocytes).

Therefore, it is expected that resorbable cements will engage in the process of bone tissue formation (i.e., dissolution through the action of the osteoclasts, followed by replacement with natural bone tissue through the action of the osteoblasts, eventually becoming replaced by naturally formed bone tissue). It is not known if the resorbable cements will be entirely resorbed. However, even in the event that the cements are not completely resorbed and that they are not entirely substituted by new bone, in view of the strength of the cements that we have discovered and demonstrated in accordance with the present invention, equivalent fixation will be achieved as compared to methacrylate cements that have been used in the prior art for bone fixation, with the possible added benefit of ultimate replacement by host tissue.

It has been speculated that such cements will have the added benefits of minimal toxicity and reduced inflammation, as compared to the levels that have been observed with the synthetic bone cements based on methacrylate polymers.

To my knowledge, however, no resorbable bone cement has been actually used in animals or in in vitro tests that are predictive of their utility in animals in the context of the use of resorbable cements to temporarily fix a bone or a device to a bone. We, however, have now discovered that such cements are indeed useful and will function in animals for temporary fixation. Furthermore, we have demonstrated that such cements in many cases exhibit equal or better strength over methacrylate cements in general, and polymethylmethacrylate (PMMA) cements in particular, and offer extreme versatility.

What is critical to the method of the invention is that cement provide fixation between an implant and the bone that is of sufficient strength and duration to withstand physiological loads while the healing process ensues. Once the bone is healed, it is preferred that the fixation weaken so that the bone, without augmentation carries those physiological loads. This allows the bone to return to health in a shorter period of time. Further, it also provides the versatility to remove the implant is desired.

Accordingly, we shall describe below the methods in which we have discovered that the resorbable cements will function with efficiency as a replacement for methacrylate polymer cements (or its derivatives) and in interlocking nail techniques.

B. General Procedure For Providing Temporary Fixation of a Device Within a Bone

As discussed above, the primary process for repairing a femur that has undergone an extensive fracture, and which appears incapable of maintaining anatomic alignment without internal support, has been the use of interlocking an intramedullary device with screw at both the proximal and distal end. However, as was discussed above, interlocking of the distal end is extremely difficult. As was also discussed above, it is possible to permanently affix a rod within the bone. However, this is not preferred because the bone tissue is never again required to carry its natural load.

Accordingly, referring now to FIG. 1, there is provided a cross-sectional view of a fractured femur after repair in accordance with the present invention. This view provides a preferred embodiment of the present invention to demonstrate its superiority in distal fixation. It will be seen that a femur 10 with a fracture 11 has an intramedullary device 13 implanted within its intramedullary cavity (not shown) and within the cancellous tissue 12 of the femur 10. The intramedullary cavity is a hollow section within the cancellous tissue 12 of the femur 10. The intramedullary device 13 has a bore 14 from its proximal end 15 to its distal end 16.

The intramedullary device 13 is typically inserted into the bone through a hole that is reamed or drilled in the cortical layer of the femur 10. The distal end 16 of the intramedullary device 13 is preferably inserted through the hole in the cortical layer of the bone and pushed or hammered downward through the cancellous tissue 12 of the femur 10 and through the intramedullary channel toward the distal channel section of the femur 17. The reamer may be used to drill through and hollow out the canal.

Advantageously, prior to the insertion of the intramedullary device 13, the intramedullary channel can be aspirated and/or lavaged to remove some or all of the marrow and loose materials contained therein. One reason for aspiration and/or lavage is to avoid fat embolus caused by the impaction of materials with high fat content against the cancellous tissue. If accomplished correctly, the aspirated materials can be saved for reuse in combination with the cement. Lavage can be accomplished with any number of physiologically acceptable solution, such as phosphate buffered saline or physiological saline.

Once the interlocking nail 18 has been inserted, a resorbable cement 23 is injected by use of a syringe 24 (or other suitable device) through the bore 14 in the proximal end 15 of the intramedullary device 13 so that the cement is communicated through the bore 14 to the distal end 16 of the intramedullary device 13 into the distal channel section of the femur 17. In a rod with transfixion holes (not shown), a special nozzle can be used to ensure that cement is not communicated out through the transfixion holes into the intramedullary canal. One such nozzle is shown in FIG. 10 and will be discussed below.

Preferably, enough cement is injected so as to fill the distal channel section of the femur 17, i.e., filling the void areas in the surrounding cancellous tissue. Typically, the effective amount of the cement will be dependent upon the volume of the bore 14 and the area at the bottom of the distal channel section of the femur 17. In normal circumstances, 30 cubic centimeters of cement will be adequate, or in certain circumstances 2 to 3 times this amount may be required.

As will be seen, the proximal end 15 of the intramedullary device 13 is secured with an interlocking screw 18. The securing with the interlocking screw 18 of the intramedullary device 13 is accomplished by drilling a hole from a position located on the greater trochanter 19 of the femur 10 to a position near the lesser trochanter 20 of the femur 10. Generally, the interlocking screw 18 has a head 21 and a spike 22. The hole from the position on the greater trochanter 19 to the position on the lesser trochanter 20 of the femur is accurately drilled so as to ensure that the hole extends through the intramedullary device 13. The intramedullary device can additionally have aiming holes (not shown) in which case the hole must be aligned through the aiming holes.

Once the cement has been injected to fill the distal channel section of the femur 17 and the intramedullary device 13 is interlocked on the proximal end 15 with the interlocking screw 18, the cement is allowed to set while the wounds are closed and the patient is awakened. As soon as the cement is set, the resorbable cement acts to secure the distal end 16 of the intramedullary device 13, acting similarly to having one or more interlocking screw(s) on the distal end 16.

Significantly, however, the process avoids three major problems with conventional intramedullary device fixation. The first problem, discussed above, is the problem associated with aiming required to place a screw through the distal portion of the intramedullary device and the bone. As was mentioned, the use of long lever arms that make aiming very difficult and have, therefore, proven unworkable. Secondly, because of the extreme difficulty and accuracy required to drill through the distal portion of the intramedullary device, fluoroscopic monitoring is required, often for prolonged periods. This exposure to radiation poses a hazard to both the surgical team who must place their hands close to the radiation beam. Thirdly, where cements were used in the prior art to aid in fixation of intramedullary devices, such cements were non-resorbable methacrylate polymers (or its derivatives). As such, and as mentioned above, they often caused tissue damage on introduction (due to heat or toxicity), and/or caused inflammation. Further, such cements are permanent and cannot be removed if the intramedullary device is to be removed, for example, if the device is misaligned.

In contrast, the resorbable cements contemplated in accordance with the present invention do not suffer from the disadvantages associated with the synthetic polymer cements, such as methacrylate (or its derivatives). Fundamentally, since such cement is resorbed or absorbed by the tissues surrounding the implant, the bond, while not permanent, is sufficiently strong to maintain fixation while allowing the fracture to heal. The rod can still be removed and replaced if misaligned or for any other reason. Further, such cements are significantly less toxic and appear to cause fewer inflammatory difficulties. Moreover, unexpectedly, such cements exhibit superior strength in compression and torsion, as compared to methacrylate polymers or their derivatives.

Most fundamentally, upon resorption, such cements lose their fixation strength between the intramedullary device and the bone. Accordingly, the bone is required to assume its natural load, without the augmentation provided by intramedullary device. In the alternative, where continuous augmentation from an intramedullary device is desired, the device can be constructed to allow ingrowth between the bone and the device, as will be appreciated by one of skill in the art.

The general technique of the present invention is also applicable to a variety of orthopedic applications. For example, referring now to FIG. 2, there is provided a cross-sectional view of a femur in which the neck portion on which the head is located is fractured. It will be observed that the femur 10 has a fracture 25 in the neck portion 26 that connects the head 27 to the femur 10. A sliding hip screw 28 having a proximal end 29 and a distal end 30 with a bore 32 extending therebetween, extends from a first position 31 on the shaft of the femur 10 just below the greater trochanter 19 to a second position 33 within the area defined by the head 27 of the femur 10. The cancellous tissue 34 around the second position 33 is relatively hollow, forming a distal channel section in the head 35 surrounding the distal end 30 of the hip screw 28.

As with the discussion of FIG. 1, when a resorbable cement is injected through the bore 32 of the hip screw 28 into the distal channel section in the head 35, it will provide a temporary fixation of the distal end 30 of the hip screw 28 within the area defined by the head and fovea 27 of the femur 10. While securing the distal end 30 of the hip screw 28, the cement is then capable of resorption, as discussed above, allowing osseous ingrowth from the cancellous tissue 34.

The distal end 29 of the hip screw 28 may be secured through any of variety of techniques that are well-known in the art. For example, two possible designs are disclosed in U.S. Pat. Nos. 4,494,535 and 4,653,489.

As will be appreciated, the exceptional advantage provided by the techniques of the present invention is that the cements contemplated by the present invention will be partially or completely resorbed or absorbed by the bone tissue that surrounds the implant allowing either removal of the device or osseous ingrowth with the implant or growth near the implant without callous or membranous growth proximate to the implant. In sharp contrast, as was discussed above, one problem encountered with the use of synthetic polymers as cements has been that certain deleterious consequences have been observed from the body's interaction with the synthetic cements. For example, these materials are not absorbed by the body after they have cured, but rather, are enveloped by the bone tissue as it grows into place.

The particular choice of resorbable cement is not entirely critical. In a preferred embodiment, however, a powder containing hydroxyapatite, orthophosphoric acid, calcium carbonate, and calcium hydroxide are reacted with aqueous alkali to form a paste as described in U.S. Pat. Nos. 4,880,610, 5,047,031, 5,053,212, and 5,129,905 all to Constantz (the disclosures of which are hereby incorporated by reference). In another preferred embodiment, compositions based on a calcium salt filler, poly-(propylene fumarate), N-vinyl-2-pyrrolidone, and a peroxide or free radical initiator used to initiate cross-linking. See U.S. Pat. No. 4,722,948 to Sanderson, the disclosure of which is hereby incorporated by reference. In still another preferred embodiment, a mixture of two calcium phosphates, tetracalcium phosphate, and dicalcium phosphate is used. See U.S. Pat. Nos. 4,612,053 (Reissue Certificate No. 33,161) and 4,518,430 (Reissue Certificate No. 33,221) both to Brown et al., the disclosures of which are hereby incorporated by reference. In still another embodiment, the materials calcium materials in combination with protein polymer units.

There are a variety of other materials that are currently proposed as resorbable cements that could operate effectively and suitably in the present invention. Moreover, there are a variety of other materials that are expected to be candidates for use in resorbable cement compositions. The focus of the present invention is not upon a particular cement. Rather, the present invention is directed towards the use of any resorbable cement that will allow temporary fixation of a device within a bone and attain the advantages described above and below.

Optionally, the resorbable cement may also contain certain active agents that will assist in, among other things, preventing or mitigating infection, enhancing bone growth in the area around the implant, increasing blood supply to the area, and treating or killing surrounding cells or tissues. One advantage observed from this technique is that the cements form a natural sustained release body; i.e., the mass of cement is slowly dissolved, and will gradually release the active agent.

Accordingly, it will be understood that antibiotics may be incorporated into the resorbable cement to prevent or mitigate infections. Also, as will be appreciated, one can enhance bone growth in area surrounding an implant through the use of a number of agents.

For example, parathyroid hormone can be incorporated into the cement to spur the development of osteoclasts in the surrounding tissue. Similarly, 1,25-dihydroxycholecalciferol can be incorporated into the cement to enhance calcium ion transport across osteoblast and osteoclast cell membranes. Each of parathyroid hormone and 1,25-dihydroxycholecalciferol will have the net effect of enhancing the resorption of the cement (i.e., each of the compounds enhance the osteoclast activity), causing enhanced pitting on the surface between the cement and the cancellous tissue in the bone. Or, calcitonin can be administered with the cement to reduce osteoclast activity and enhance osteoblast activity or bone morphogenic protein that assists in the growth of new bone. The net effect being greater bone growth at the cement/cancellous tissue surface.

Vasoactive agents may generally be thought of as members of a class of compounds that enhance the permeability of the microcirculatory system, promoting, among other things, oxygen transfer. As such, vasoactive agents can be suitably admixed into the cement, prior to administration, so as to enhance the microcirculatory architecture of the growing cancellous tissue around the implant. Suitable agents include certain of the interleukins (i.e., IL-1, IL-2), and many others.

In addition, in certain situations, where cancerous growth is present or indicated in the bone tissue, it could be advantageous to incorporate antitumor compounds into the cement. Often, the methods and techniques of the present invention are useful and/or indicated in preventative orthopedic situations where a patient with a bone cancer is expected to develop microfractures. There, the techniques of the present invention assist in augmenting bone structure. With the incorporation of antitumor compounds, there will be observed the effect of gradual remission of the cancerous cells surrounding the implant, followed by generally normal growth of the cancellous tissue progressively towards the implant. A similar technique was suggested in U.S. Pat. No. 4,653,487, mentioned above, where the natural toxicity of synthetic cements was expected to aid in causing remission in cancerous cells in bone.

Of course, analogues and active fragments of the above mentioned types of active agents can also be suitably administered.

C. The Preferred Method to Accomplish Temporary Fixation

To understand the particular methods to accomplish temporary fixation within the broad objectives of the present invention, we provide a discussion of distal fixation of an intramedullary device in accordance with a preferred embodiment of the present invention. Reference is made to FIGS. 3 through 7, where there are provided a series of cross-sectional views of a femur with a fracture that is repaired in accordance with the present invention. As well, FIGS. 3a through 6a represent elevational cross-sectional views taken along lines 3a through 6a of FIGS. 3 through 6 showing in detail how the cement fills the distal portion of the femur for temporary fixation of an intramedullary device in accordance with the present invention.

In FIG. 3, there is shown a femur 10 with a complete fracture 11. As will be appreciated, a clean fracture is depicted for convenience, however, the fracture could be comminuted or otherwise contain smaller fragments of bone. Also visible is the intramedullary cavity 36 which is a hollow area of the femur 10 within the cancellous tissue that extends from a position somewhat distal and below the lesser trochanter 20 to a position just proximal of, and under, the patellar surface (not shown). The intramedullary cavity 36 is generally filled with bone marrow, and is not very solid.

In FIG. 3a, which is a cross-sectional elevational view of the femur 10 taken along line 3a—3a in FIG. 3, the intramedullary cavity 36 can be seen surrounded by cancellous tissue 12.

Continuing on in the method of the present invention, in FIG. 4, the fracture 11 in the femur 10 is aligned and the bone is brought together and the position maintained by conventional techniques. Thereafter, a hole 37 is drilled in the cortical layer of the bone in its proximal end 38. It will be appreciated, depending on the severity of the fracture, a guiderod or guidewire can be inserted into the hole and directed through the intramedullary canal toward the distal channel section. Such a guiderod or guidewire will assist in aligning the proximal and distal ends of the bone, as well as facilitating the directing of a rod through the hole. The hole may continue to be drilled and/or reamed from a proximal end 38 of the femur 10 between the greater trochanter 19 and the neck section 26. Depending on whether a guiderod or guidewire is used, this can be accomplished either over-the-wire or rod, or not. The hole 37, generally, extends to a distal position 39 near the distal end 40 of the femur 10. It is preferable that the hole 37 be drilled in the cortical layer of the bone then the rod 13 (FIG. 5) is inserted along the length of the femur 10 toward the distal position 39. Again, this may be accomplished either over-the-wire or rod, or not. In the following discussion, we will refer to the drilling and reaming as "reaming."

In general, the distal position 39 of the hole 37 is located between 10 and 30 millimeters proximal of the distal end 40 of the femur 10. The actual distance from the distal end 40 of the femur 10 is not highly important, provided, of course that the knee surface (not shown) is not reached or interfered with. However, the hole 37 should be distal enough so that the distal position 39 of the hole 37 extends into the cancellous tissue 12 near the distal end 40 of the femur.

In drilling the hole 37, it will be seen, in FIG. 4a which is a cross-sectional elevational view of the femur 10 taken along line 4a—4a in FIG. 4, that the hole 37 is circular in cross-section, and as can be seen clearly in FIG. 4, it is of substantially the same diameter from the proximal end 38 to the distal position 39, providing a clear path for the insertion of an intramedullary device. The diameter of the hole 37 should be about the diameter of the intramedullary device that is intended to be inserted, so that a snug fit is obtained, but could also be larger than the intended rod.

In the next step, referring now to FIG. 5, an intramedullary device 13 is inserted into the hole in the proximal end 15 of the femur 10, and usually tamped distally through the hole with a hammer, until the distal end 16 is just proximal of the distal position 39 in the channel opening 41 in the femur 10. The channel opening 41 is composed of cancellous bone which is somewhat vacuous normally. In this way, the intramedullary device 13 spans the fracture 11 and will soon provide axial and torsional rigidity to the fracture 11. As will be seen in FIG. 5a, which is a cross-sectional elevational view taken along line 5a—5a in FIG. 5, the intramedullary device 13 is located relatively concentrically within the channel opening 41 and the bore 14 will soon provide the mechanism for the resorbable cement to enter the distal channel section 41.

Accordingly, in FIG. 6, the resorbable cement is injected through the bore 14 in the intramedullary device 13 from its proximal end 15 to its distal end 16, through the injection device 24, so as to fill the channel opening 41 with the resorbable cement. The resorbable cement is injected in a sufficient amount to ensure that there are few, if any, voids in the distal channel section 41. In FIG. 6a, which is a cross-sectional elevational view along line 6a—6a in FIG. 6, it will be seen that the resorbable cement has filled the enlarged channel opening 41, providing boundary layers 12a and 13a between the cement and the cancellous tissue 12 and the intramedullary device 13, respectively. Usually, at this stage the femur 10 will again be checked to ensure that the alignment of the fracture 11 is correct.

For fixation of the proximal end of the intramedullary rod, as was described above, it is conventional to mechanically connect or link the proximal end of the rod in a fixed position to the bone with a screw. In general, a jig is used to position a drill bit to drill through the bone and the rod. Accordingly, in FIG. 7, nearing the completion of the method of the present invention, a drilling jig 42, having an upright 43, an outrigger 45, a side piece 44, and a core drill 46 is positioned on the proximal end 15 of the intramedullary device 13. A slidably mounted reference probe 48 is positioned to slide into the bore 14 of the intramedullary device 13 through the upright 43. The core drill 46 is angularly mounted onto the side piece 44. In this manner, a hole may be accurately drilled from an appropriate position on the greater trochanter 19 to the lesser trochanter 20 and pass through the intramedullary device 13 to allow the insertion of an interlocking screw (not pictured). In some embodiments, it is possible to use an intramedullary device 13 having side ports 47a and 47b positioned in the path that the core drill will take to minimize drilling difficulty. The precise angle at which the core drill 46 in the side piece 45 is preset in the drilling jig as is well known to those of skill in the art.

Referring back now to FIG. 1, the interlocking screw 18 is inserted through the holes that are drilled in the previous section to finalize the repair of the fracture 11. As will be appreciated, the above discussed method may be accomplished relatively quickly and with significantly less fluoroscopic imaging than is required for distal insertion of interlocking screws and with far fewer toxic and permanent effects than permanent cementing.

Figure 9:
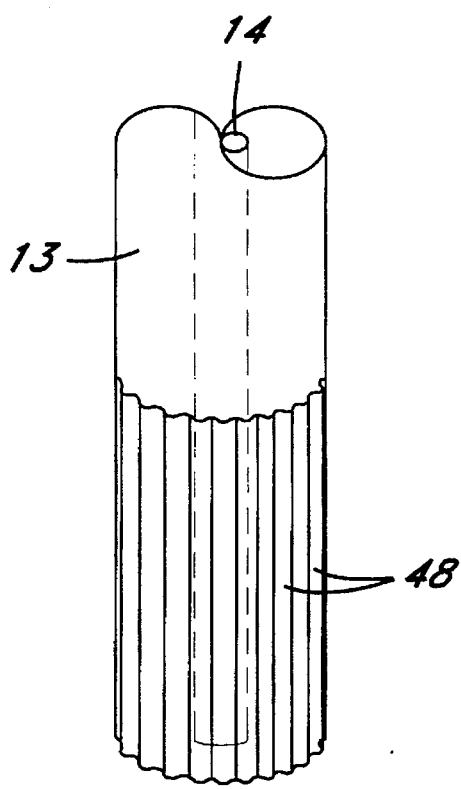

Thus, in FIG. 9, there is provided a fin design that can be used to enhance the strength of the intramedullary device 13 in torsional loads as well as promote ingrowth. It will be seen that the intramedullary device 13 has the bore 14 running from its proximal end (not shown) to its distal end 16, but, is provided with a plurality of grooves 48 in the very distal end 16. When cement is injected through the bore 14, the grooves 48 will be surrounded by the cement. As such, the grooves 48 aid in preventing torsional forces being translated into movement of the device. At the same time, however, the grooves 48 do not provide for additional binding in a longitudinal direction beyond the strength of the bond between the shaft and the cement. This allows the shaft to be withdrawn when desired or necessary.

A conventional cloverleaf design of a rod can also be used in the present invention. Such rods are used extensively in orthopedics. They provide the advantage of having an irregular external geometry that increases their ability to withstand rotational forces, but do not prevent removal when a longitudinal force is applied. In particular, strength in rotation is enhanced, especially if the rod has a closed cross section. Current designs have a flute running the length of the rod that decreases rigidity but facilitates insertion.

Generally, the intramedullary device will be constructed of stainless steel or an equivalently strong, inert, and physiologically acceptable material. Titanium is another example of a suitable material for use in intramedullary rod construction. Cobalt chrome can also be used as the construction material for the intramedullary devices of the present invention.

As discussed in connection with FIG. 7, the step of interlocking the proximal end of the rod can be accomplished with a rod having side ports 47a and 47b. The side ports 47a and 47b are aligned on the correct angle so that the surgeon does not have to drill through the rod. Rather, the surgeon only has to drill from the appropriate position on the greater trochanter 19 to the lesser trochanter 20 and pass through the side ports 47a and 47b on the intramedullary device 13 to allow the insertion of an interlocking screw (not pictured). However, when cement is to be injected through the device, it is preferable to have the cement bypass the side ports 47a and 47b so that the cement is not communicated out through them.

In FIG. 10 there are provided a series of views of a bypass nozzle that allows the injection of cement through an intramedullary device without the cement passing through the aiming holes or side ports. In FIG. 10a, there is provided front and back top perspective views of the bypass nozzle 49 of the present invention. The bypass nozzle 49 is of generally tubular construction with a shaft 50 having a proximal end 51 and a distal end 52. On the proximal end 51, there is a connector housing 53. The connector housing 53 is constructed with an open end 54 and a receptacle 55. The open end 54 is designed to connect or attach to or with an injection device (not pictured). The receptacle 55 is constructed to attach or connect with the proximal end of an intramedullary device (not pictured). Extending from the proximal end 51 of the shaft 50 inside the connector housing 53 in the open end 54 to the distal end 52 of the shaft 50, there is a lumen 56.

As will now be appreciated, an injector device can be attached or connected to the bypass nozzle 49 in the open end 54 of the connector housing 53 and cement can be injected through the lumen 56. Another view of the construction of the bypass nozzle 49 can be seen in FIG. 10b which is a cross-sectional view of the bypass nozzle 49. In this view, the lumen 56 can be seen clearly extending from the distal end 52 to the proximal end 51 of the shaft 50. The lumen 56 terminates at the proximal end 51 of the shaft 50 in the connector housing 53 inside the open end 54. The open end 54 is constructed to receive an injection device (not shown). Also clearly seen is the receptacle 55 which opens distally to receive the intramedullary device (not shown).

In FIG. 10c, the bypass nozzle 49 is shown in cross section in place in an intramedullary device 57 also shown in cross section. The bypass nozzle 49 sits on the proximal end 58 of the intramedullary device 57 with the receptacle 55 receiving the proximal end 58, and preferably sealing around the proximal end 58. The shaft 50 of the bypass nozzle 49 extends through the bore 59 in the intramedullary device 57 so that the distal end 52 of the bypass nozzle extends past the side ports 60a and 60b in the intramedullary device 57.

Also shown in FIG. 10 is an injector device (a syringe 61) about to engage with the connector housing 53 in the proximal end 51 of the bypass nozzle 49. The syringe 61 has a tip 62 that is sized to fit (and preferably connect with) the connector housing 53. Once connection is made between the tip 62 and the connector housing 53, cement 63 can be pushed and injected from the syringe 61 through its tip 62 by pushing on plunger 64. The cement will travel from the tip 62 through the lumen 56 and out the distal end 52 of the shaft 50 of the bypass nozzle 49 and into the bore 59 of the intramedullary device 57. However, the cement will bypass the side ports 60a and 60b.

The open end 54 of connector housing 53 of the bypass nozzle 49 can be equipped with a standard locking type attachment or any other connector of functional equivalence, such as tight slip or friction fits, other threaded arrangements, and the like. It is preferable that the open end 54 form a seal with any injector device that is used, since the connection therebetween will be under pressure while cement is injected into a bone through the lumen 56 and the bore 59.

It will be appreciated that receptacle 55, although typically has a circular configuration as shown here, can have any geometry chosen. For example, often cloverleaf intramedullary designs are used. While the receptacle 55 would typically be constructed as a circular bore, in the event it was constructed without a circular bore, the receptacle 55 will preferably have such geometry or be capable of fitting such geometry. This can be accomplished through appropriate molding or machining of the bypass nozzle or the connector housing. Or, in the alternative, the receptacle can be formed of a substantially flexible material that will conform to the appropriate geometry and preferably form a substantially sealing engagement. One example of a material that will meet these criteria is a rubber, such as a silicone rubber. In such a situation, the receptacle will act in a "septum" like capacity.

The bypass nozzle 49 can be constructed of any suitable materials. Preferably, the bypass nozzle is formed of a material that can be sterilized and is sufficiently rigid to be pushed into the bore 59 of the intramedullary device 57. However, the bypass nozzle should be sufficiently flexible to resist breakage and conform and substantially seal the bore 59. Further, the receptacle 55 and the open end 54 of the connector housing 53 should be capable of forming sealing fits with the proximal end 58 of the intramedullary device 57 and the injector device (such as the syringe 61), respectively. For example, a variety of plastic or polymer materials possess these characteristics. One such material that is highly advantageous is ultrapure polypropylene. Also, a variety of materials have been shown to be useful in the preparation of intravascular catheters such a polyethylene, polyimide, polyvinyl chloride, polyesters and composite materials. The bypass nozzle 49 can be formed by conventional techniques, e.g. extruding. It can be formed in one piece (i.e., molded) with connector housing 53 or the connector housing 53 can be joined by suitable adhesive such as the acrylonitrile based adhesive sold as Loctite TM 405. Heat shrinking can also be employed where appropriate.

It is also preferable that the material be strong enough so that the lumen 56 can be of maximum diameter. Maximizing the inner diameter of the lumen 56 facilitates the cement injection through the lumen 56. The optimal construction materials of the bypass nozzle 49 to meet the foregoing objectives will be readily understood to those of skill in the art and cement introducer devices meeting these objectives can be prepared without undue experimentation.

It will be appreciated that the intramedullary devices for use in the present invention can be solid or hollow. Hollow is preferred, since the hollow channel can be used to inject the cement. However, there are advantages attendant to the use of solid devices, such as increased strength. Where a solid device is to be used, a cement introducer device can be inserted linearly through the bone and cement injected therethrough. An advantage to this procedure is that the introducer can typically have a larger inner diameter than the bore 14 in a hollow intramedullary device. Thus, cement can be more easily introduced and delivery of greater quantities of cement to the bone, in a given time, can be effected.

This use of a cement introducer device is especially useful in thin or narrow bones, where a small diameter intramedullary device is typically used. As will be understood, this technique may also be used in connection with either hollow or solid intramedullary devices.

Figure 11:
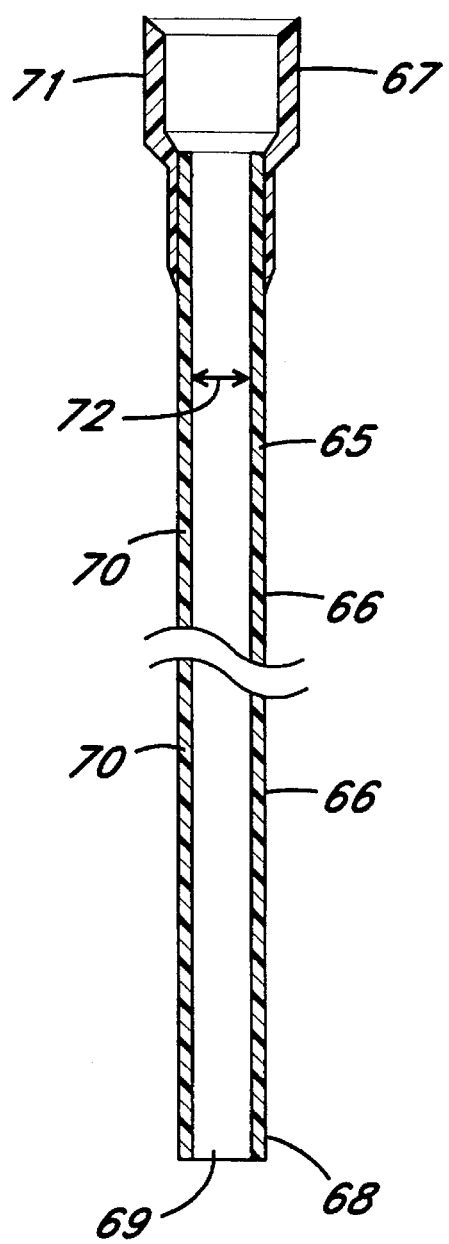
Figure 12:
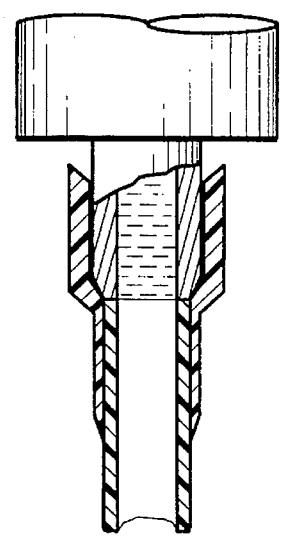

An example of a cement introducer device is shown in FIG. 11. Typically, the cement introducer device 65 is of flexible tubular construction having a shaft 66 with a proximal end 67 and a distal end 68 and a lumen 69 extending therebetween. The cement introducer device has an outer wall 70. The proximal end 67 of the cement introducer device 65 is constructed with a connector housing 71 to allow an easy, yet sealed attachment or connection to or with an injector device, such as a syringe. An example of the cement introducer device attached to a syringe is shown in Figure 12. Returning to FIG. 11, the connector housing 71 on the proximal end 67 of the cement introducer device 65 can be a standard locking attachment or any other connector of functional equivalence, such as tight slip or friction fits, other threaded arrangements, and the like. It is preferable that the connection seal, since the connection will be under pressure while cement is injected into a bone through the lumen 69.

The cement introducer device 65 can be constructed of any suitable physiologically acceptable materials. For example, they can be constructed of thin gauge metals to enhance pushability yet retain flexibility. Alternatively, they can be constructed from a variety of plastic or polymer materials. One such material that is highly advantageous is ultrapure polypropylene. Also, a variety of materials have been shown to be useful in the preparation of intravascular catheters such as polyethylene, polyimide, polyvinyl chloride, polyesters and composite materials such as described in U.S. Pat. No. 4,981,478 (Evard et al.) which is incorporated herein by reference. The shaft 66 of the cement introducer device 65 can be formed by conventional techniques, e.g. extruding. The connector housing 71 can be either formed in one piece (i.e., extruded) with the cement introducer device 65 or can be joined by suitable adhesive such as the acrylonitrile based adhesive sold as Loctite TM 405. Heat shrinking can also be employed where appropriate.

The optimum material for the construction of the cement introducer device is one that allows maximum pushability, but that has sufficient flexibility and deformability to be easily worked through the interior of a bone. Moreover, it is preferable that the material be strong enough so that the wall 70 can be thin to allow a maximum inner diameter 72 of the cement introducer device. Maximizing the inner diameter 72 facilitates the cement injection through the lumen 69. The optimal construction materials of the cement introducer device 65 to meet the foregoing objectives will be readily understood to those of skill in the art and cement introducer devices meeting these objectives can be prepared without undue experimentation. In addition, an obturator can be inserted into the cement introducer to stiffen it and ease the insertion of the cement introducer. Or, the obturator can serve an additional purpose of acting as a guiderod over which the inner lumen of the cement injector is passed.

In use, referring to FIGS. 13a and 13b, a bone, such as a femur 10 is prepared essentially as discussed in connection with FIGS. 3 through 4. Once the hole 37 (FIG. 4) is drilled in the proximal end 38 of the femur 10 through the cortical bone, and the intramedullary canal 36 becomes accessible, the distal end 68 of the cement introducer device 65 can be threaded distally through the intramedullary canal 36, until it reaches the distal channel section of the femur 10.

Figures 13A, 13B:
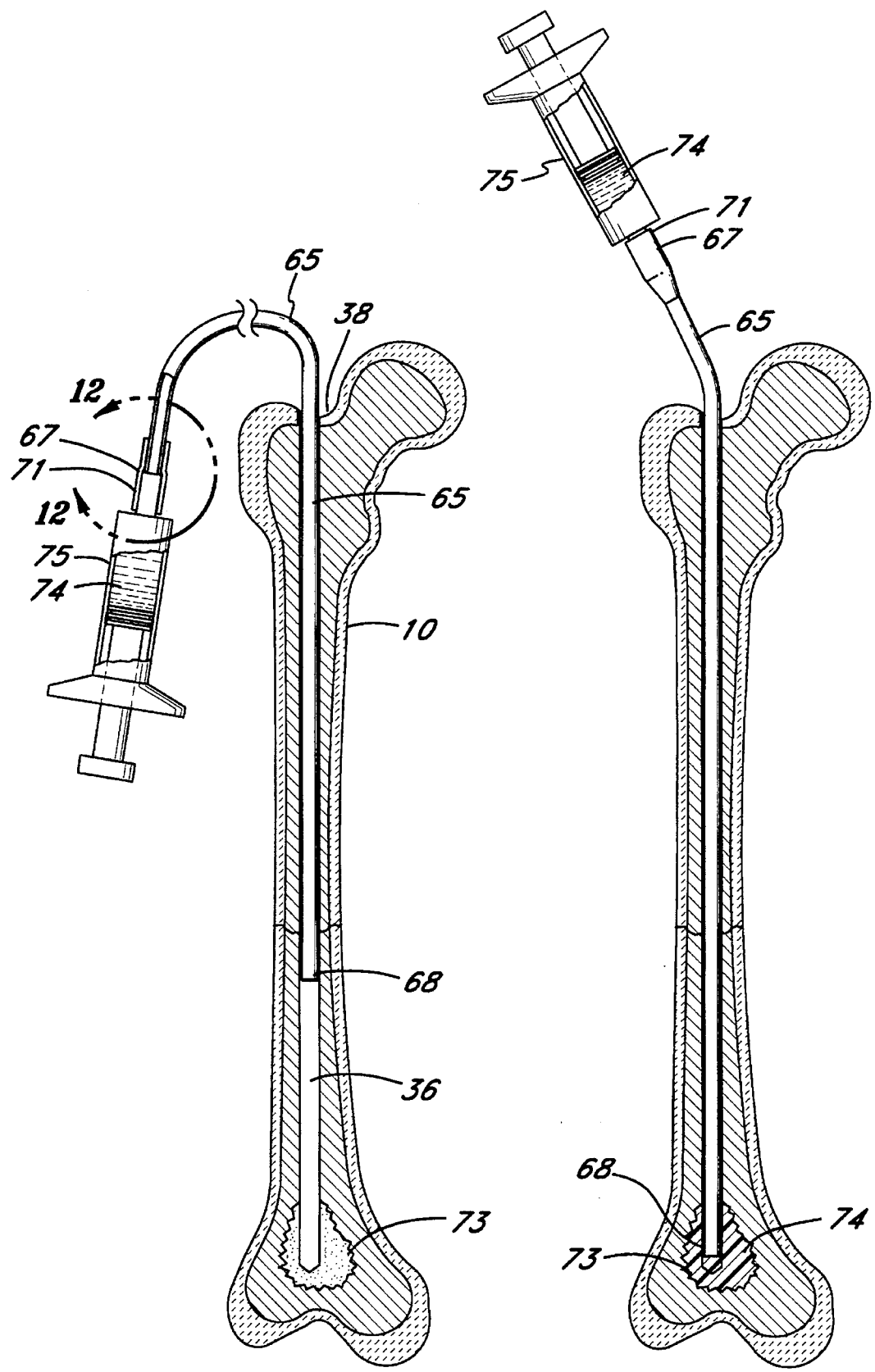

In FIG. 13b, once the distal end 68 of the cement introducer device 65 is in position in the distal channel section 73 of the femur 10, cement 74 is injected from the syringe 75 to fill the cancellous tissue surrounding the distal channel section 73 of the femur 10. It will be appreciated that the syringe 74 can either be attached while the cement introducer device 65 is being threaded through the intramedullary canal 36, or, it may be attached to the connector housing 71 in the proximal end 67 of the cement introducer device 65 when its distal end 68 is in position in the distal channel section 73 of the femur 10.

Thereafter, the rod may be slipped into the bone through the cement injector tube and the proximal end interlocked (see FIGS. 5–7). The cement introducer device 65 may either be removed prior to the rod's insertion or after but preferably after to act as a guide for, and ease the sliding of, the rod during insertion. Further, the introducer device can assist in reduction of the fracture through aiding in maintaining alignment of the bone. In any event, the cement introducer device 65 is preferably removed prior to interlocking (see FIG. 7). The rods in this application would ordinarily be solid for greater strength since their diameter would be smaller than a traditional hollow rod.

As was mentioned above, it is advantageous to aspirate and/or lavage the intramedullary canal prior to insertion of the rod or injection of the cement. This reduces the possibility that high fat content materials will be impacted into the cancellous tissue and cause fat embolism. The cement introducer device can double in this function; first being used for aspiration and/or lavage, followed by injection of the cement.

As will be appreciated, because the resorbable cements contemplated in accordance with the present invention are preferably absorbed by the bone tissue through osteoclast action (i.e., the cements are dissolved), followed by new bone tissue deposition, the cement merely provides a temporary platform to enable the new bone to be deposited around the intramedullary device. Critical to the success of the process are the health of the tissue (both near the distal end and around the fracture) and the expected loads over time.

Preferred resorbable cements for use in the present invention are made commercially by, among others, Norian Corporation, Mountain View, Calif., DynaGen, Inc., Cambridge, Mass., OsteoGenics, Inc., and Protein Polymer Technologies, Inc. (all of these products are still experimental).

Each of these available cements use different chemical compositions. The Norian materials are based on compositions of hydroxyapatite, phosphoric acid, calcium carbonate, and calcium hydroxide. See U.S. Pat. Nos. 4,880,610, 5,047,031, 5,053,212, and 5,129,905 all to Constantz, the disclosures of which are hereby incorporated by reference. The DynaGen materials are based on compositions of a calcium salt filler, poly-(propylene fumarate), N-vinyl-2-pyrrolidone, and a peroxide or free radical initiator used to initiate cross-linking. See U.S. Pat. No. 4,722,948 to Sanderson, the disclosure of which is hereby incorporated by reference. The OsteoGenics compositions are essentially a mixture of two calcium phosphates, tetracalcium phosphate, and dicalcium phosphate. See U.S. Pat. Nos. 4,612,053 (Reissue Certificate No. 33,161) and 4,518,430 (Reissue Certificate No. 33,221) both to Brown et al., the disclosures of which are hereby incorporated by reference. Finally, the Protein Polymer Technologies, Inc. cements are calcium based cements.

Alternatively, cements may be prepared by the user according to any of the variety of patents or literature sources now available relating to resorbable cement materials.

D. Hip Screw Fixation

In another preferred embodiment, the invention is advantageously used in hip screw fixation (FIG. 2). The method is substantially similar to that described above for femur fixation.

In FIG. 2 there is provided a cross-sectional view of a femur in which the neck portion on which the head is located is fractured. It will be observed that the femur 10 has a fracture 25 in the neck portion 26 that connects the head 27 to the femur 10. A sliding hip screw 28 having a proximal end 29 and a distal end 30 with a bore 32 extending therebetween, extends from a first position 31 on the shaft of the femur 10 just below the greater trochanter 19 to a second position 33 within the area defined by the head 27 of the femur 10. The cancellous tissue 34 around the second position 33 is relatively hollow, forming a distal channel section in the head 35 surrounding the distal end 30 of the hip screw 28.

As with the discussion of FIG. 1, when a resorbable cement is injected through the bore 32 of the hip screw 28 into the distal channel section in the head 35, it will provide a temporary fixation of the distal end 30 of the hip screw 28 within the area defined by the head and fovea 27 of the femur 10. While securing the distal end 30 of the hip screw 28, the cement is then capable of resorption, as discussed above, allowing osseous ingrowth from the cancellous tissue 34.

The distal end 29 of the hip screw 28 may be secured through any of variety of techniques that are well-known in the art. For example, two possible designs are disclosed in U.S. Pat. Nos. 4,494,535 and 4,653,489.

E. Fixation of Other Devices/Fractures

The above discussion focuses upon the repair of fractures in the hip and in the femur. However, it will be appreciated that other devices, than those discussed above, may be suitably fixed in accordance with the present invention. For example, rods may be suitably implanted into any long bone for purposes of repair or augmentation in accordance with the method of the present invention. Moreover, it is also possible to implant prosthetic attachment devices and to place rods in the spine.

1. Rod Placement and Fixation in Single Bones

To accomplish a placement of a rod into any single bone, the same techniques will be followed as were discussed above in connection with the femur. Accordingly, an end of a bone is exposed and a channel is drilled from the exposed end to the other end. Thereafter, a hollow rod is inserted, and resorbable cement is injected through the hollow rod, so as to provide fixation between the distal end of the rod and the cancellous tissue that surrounds the rod. As mentioned above, a cement introducer device can also be used for the injection of cement. This is particularly preferred, because all of the other bones in the human body are smaller than the femur.

In this way, the rod will be fixed temporarily with resorbable cement in the distal position. Analogous steps may be taken to secure the proximal end of the rod. Or, in the alternative, the proximal end of the rod may be mechanically fixed using techniques that are well known in the art, such as interlocking nail placement, as discussed above.

2. Fixation of a Rod in the Spine

The spine is composed of a series of vertebrae. Generally, the spine consists of 24 independent vertebrae, running from the coccyx (tail bone) and the sacrum to the skull. Seven vertebrae comprise the cervical (neck) region, 12 vertebrae comprise the thoracic (chest) region, and 5 vertebrae comprise the lumbar (lower back) region. Each vertebra is separated from the ones which surround it by a disk of cartilage.

There are a number of afflictions in which various regions of the spine are deformed or experience collapse. For example, scoliosis (curvature of the spine) may occur in youngsters who are undergoing rapid growth, compressed vertebrae (due to excess loading, compression injuries, or osteoporosis), cracked vertebrae, among others. In order to repair such afflictions, it is often necessary to immobilize the spine in the area surrounding the affected vertebra or vertebrae. Typically, this has been accomplished by placement of a rod or rods, either internally in, or externally to, the vertebrae using hooks or screws to secure the rod.

In contrast, as will be appreciated by one of skill in the art, in accordance with the present invention, rods may be placed, again, either internally or externally, without the need for drilling holes to pin the rod or rods. Or, only partial pinning needs to be used.

3. Fixation of Comminuted Fractures

Comminuted fractures are fractures in which a plurality of bone fragments are produced in the break. They can occur adjacent to and extend into joint areas, in which case, they are called intraarticular. However, they may occur in any bone in essentially any position. The methods of temporary fixation of the present invention are also useful in the repair of comminuted fractures, particularly those located near the ends of bones.

Figure 14A:
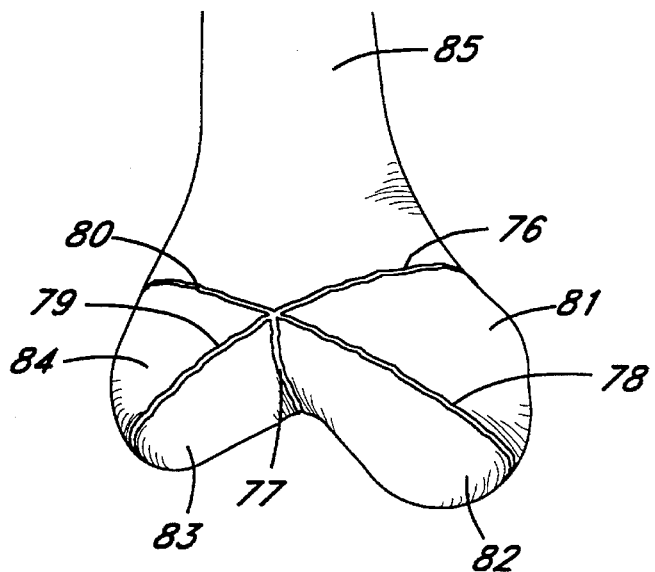
Figure 14B:
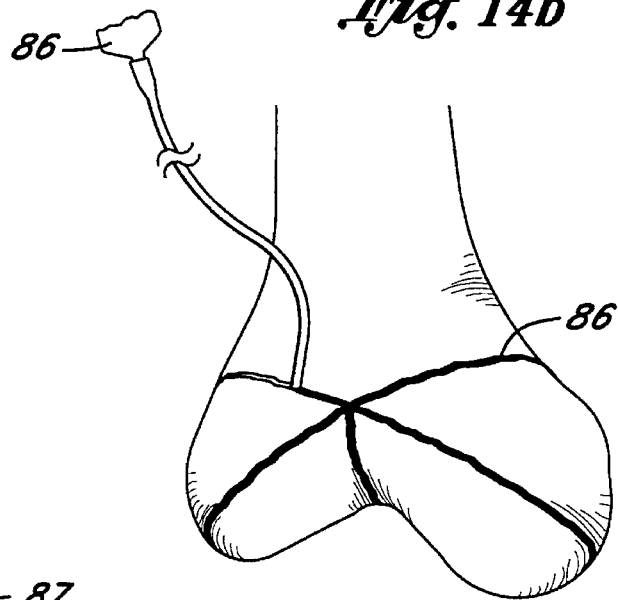

The repair of a comminuted fracture in accordance with the present invention is demonstrated in FIGS. 14a through 14d. In the Figures, an interarticular comminuted fracture is shown. Referring to FIG. 14a, a series of fractures (76 through 80) separate four fragments 81 through 84 from the main bone shaft 85. To repair such fractures in accordance with the present invention, the surgeon may first align the fragments so that they will be even upon closure of the fractures. Thereafter, a resorbable cement is injected into the fractures and worked into the bone so that there will be adequate interlock between the cement and the interior cancellous tissue (see FIG. 14a and 14b). Injection of the cement can be done manually or with the aid of an injection device, such as the syringe 86.

Figure 14C:
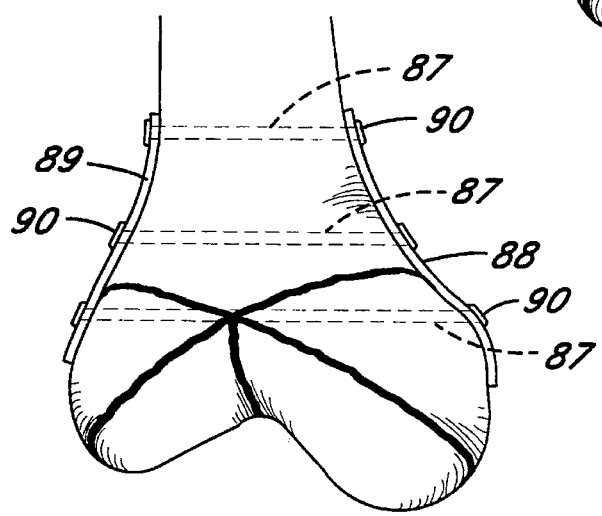

Next, the fragments are typically manually pushed together. After the fragments are cemented and moved together, they appear as shown in FIG. 14c. Thereafter, holes 87 may be drilled across and around the fracture site and the bone area fitted for contoured plates 88 and 89. The plates 88 and 89 can be secured to or through the bone with screws 90 to stabilize the fracture site as shown in FIG. 14d. In addition, or in the alternative, to stabilizing the fracture site with plates and screws, circlage can be used. However, it is important that any circlage be kept from interfering with the blood supply to the bone. Alternatively, a rod may be implanted in the cement prior to curing to achieve attachment to the remainder of the shaft.

II. EXPERIMENTAL

The following experiments were conducted in order to determine whether the use of resorbable cements could complement or enhance the effectiveness of bone repair where interlocking is indicated as necessary to accomplish repair.

EXPERIMENT I

We tested a resorbable cement against a methacrylate polymer cement (polymethylmethacrylate, "PMMA") in distal cementing of a intramedullary device. The tests were done in, first, a nondestructive fashion, in both compression, and torsion, and, then, tested to ultimate failure in torsion (the expected weakest parameter of the cement). Bovine femurs and custom made non-slotted cloverleaf rods were employed in these tests.

A. Materials and Methods

1. Preparation of Femurs

A total of six pairs of bovine femurs were tested in compression and torsion. Femurs were obtained within 48 hours of death from a local slaughterhouse. Upon removal of all soft tissue, the distal femur was cut 14 centimeters from the distal end, and the posterior, anterior and lateral portions of the condyles were trimmed to permit proper fixation in the testing jig. All bone marrow was removed from the canal of this bone segment. An intramedullary rod was then temporarily inserted to be sure it could be seated to a minimal depth of 10 centimeters. Any interfering bone in the canal was removed and the canal was washed with boiling water. Left and right femurs were designated for either PMMA or resorbable cement in a random fashion.

2. Preparation of Cement

The resorbable cement was prepared in accordance with the following Example 1, and PMMA was prepared in accordance with the following Example 2.

Example 1

We used the M828 cement commercially available from Norian Corporation in Mountain View, Calif. We prepared the cement in accordance with the manufacturer's directions.

EXAMPLE 2

A Zimmer (Zimmer, Warsaw, Ind.) polymethylmethacrylate polymer cement was prepared according to the manufacturer's instructions. See Zimmer Product Brochure No. 87-6202-301-00 (1989). Typically, the monomer solution containing methyl methacrylate monomer, N,N-dimethyl-p-toluidine, and hydroquinone is added to the solid polymer powder that contains the poly(methyl methacrylate), barium sulfate, and benzoyl peroxide. This is done so as to minimize air entrainment and increase mixing efficiency.

3. Fixation of Rods in the Femurs

In the case of either cement, the cement was hand packed and pressurized into the canal of the femur, and the intramedullary rod was inserted into the cement-femur complex until it reached a depth of 10 centimeters. The femurs were then wrapped in saline soaked gauze, double bagged in Ziploc® bags, and submerged in a water bath, which was maintained at 37° C., for 24 hours. Each bone-rod complex was placed in a refrigerator for a maximum of 24 hours before mechanical testing.

B. Testing Protocol

All mechanical testing was performed using an Instron test machine. Specimens were removed from the refrigerator prior to testing and allowed to equilibrate at room temperature while preparations were made for testing. The distal portion of the each specimen was potted in a rectangular jig and held in position by Serroban (available from Small Parts, Inc., Miami, Fla., Part No. K-LMA-158) low melting point metal. This metal conformed to the shape of the bone exactly and allowed for rigid fixation of the bone. The jig was then adjusted in the Instron testing machine to permit application of a compressive load along the shaft of the rod (FIG. 12).

Cyclic compression was performed for 10 cycles between 0 and 100N. The output of the load cell was recorded on a data acquisition system. The rod-bone complex was then reoriented and connected to a disc and cable system that permitted torque to be applied to the rod (FIG. 13). The rod was instrumented with a rotational transducer to measure the angular rotation throughout the torsion test. The rod was rotated until the measured load reached 100N and the rod was cycled in torsion between 100 and 200N for 10 cycles. Upon completion of the 10th cycle, the load was maintained at 100N while settings were made for the failure test. The rod was then rotated to failure. Failure was defined as the first drop in load, signifying a break in the bone or cement. All rotational data and load data was acquired with the data acquisition system.

C. Statistical Analysis

All statistical comparisons of the structural properties were made using an unpaired t-test with the level of significance set at $\alpha=0.05$.

1. Compression Results

Results of the compression test are illustrated for a typical specimen in FIG. 14. The figure represents the loading phase of the tenth cycle for the resorbable cement and the PMMA cement. The horizontal axis represents the crosshead deformation which took place during this loading phase, and is termed the relative deformation, in millimeters. The compressive stiffness was determined by a first order least squares curve fit. This fit included raw data between 20 and 90 Newtons. Results of all six specimens are reflected in the bar chart in FIG. 14, summarizing the compressive stiffness as the mean ± standard error.

2. Torsion Results

Figure 16:
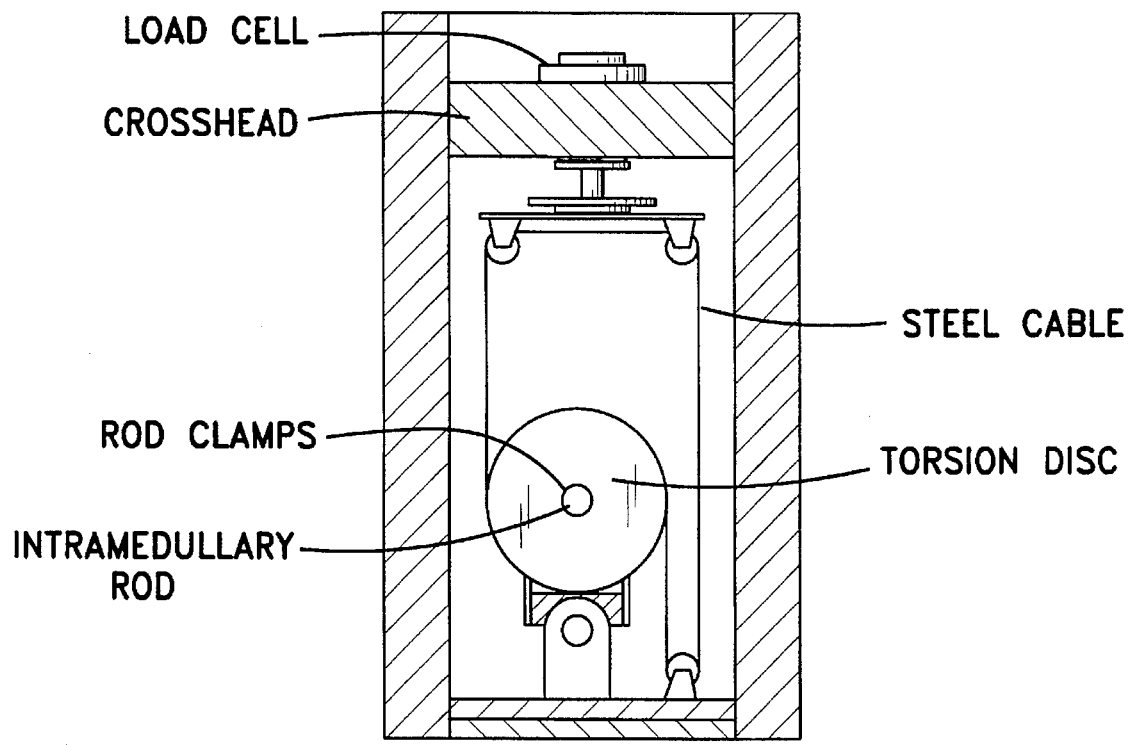
Figure 17:
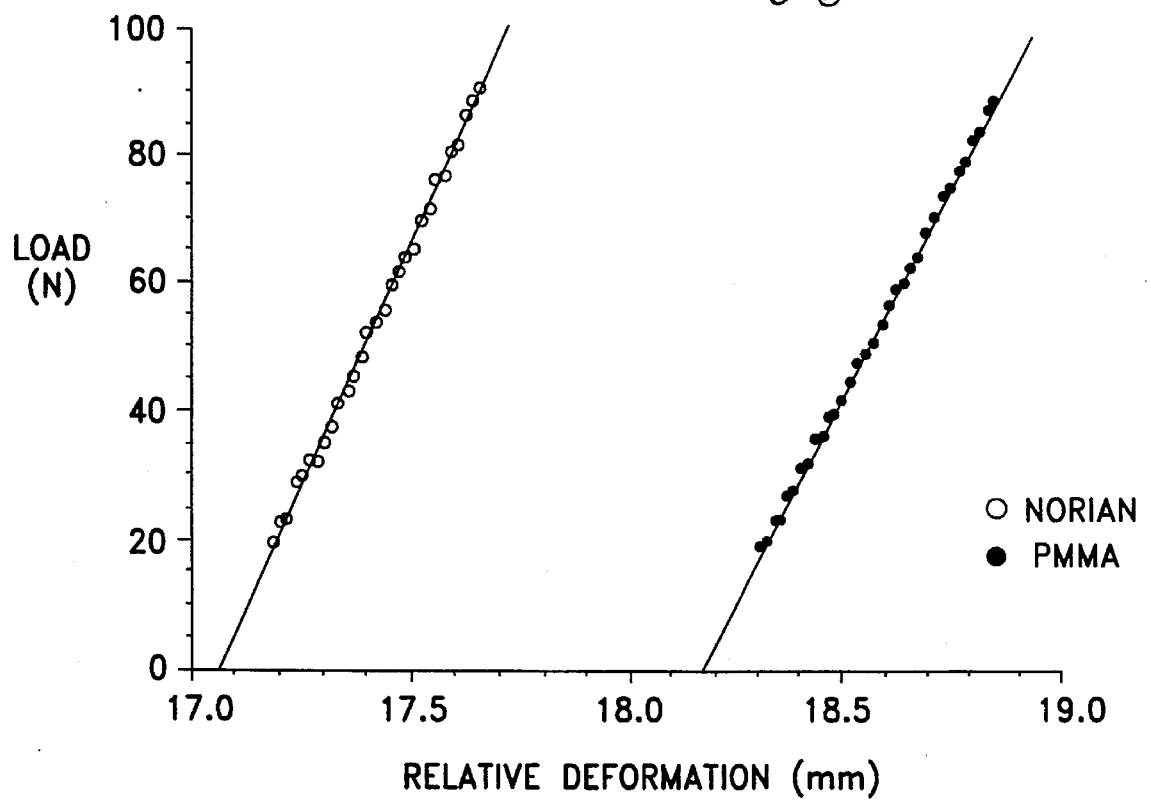
Figure 18:
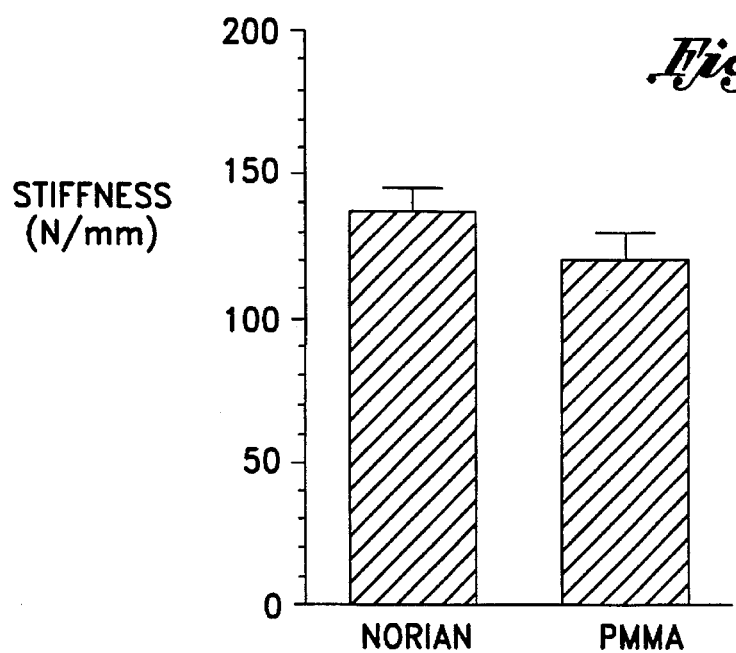
Figure 19:
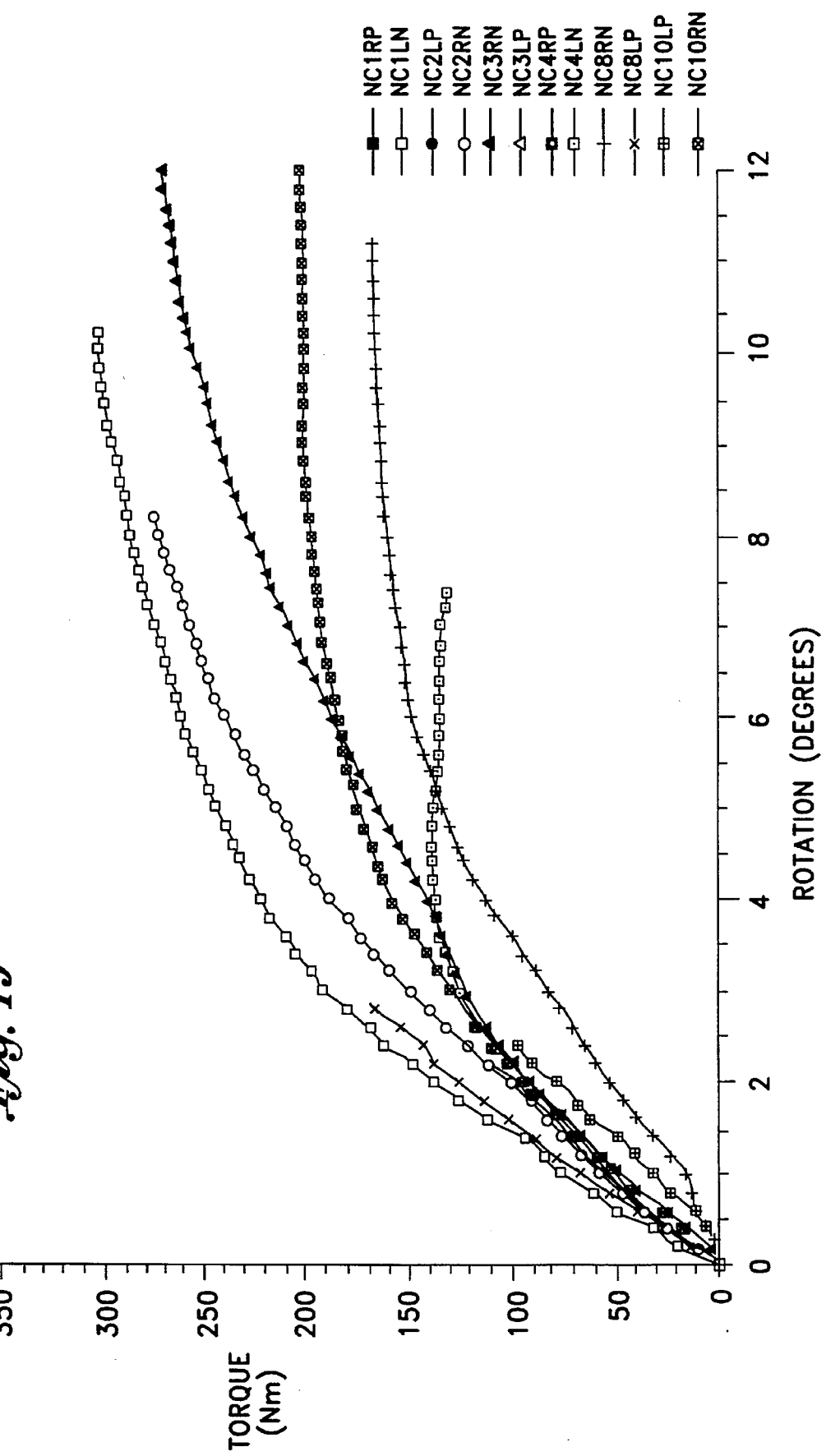

The goal of torsional testing was to test the strength of the cement. The selection of a non-slotted cloverleaf intramedullary rod was predicated on the findings in the literature (Kyle, et al., [CITE] (1985); Covey, et al., [CITE] (1990)) that closed rods displayed increased torsional rigidity when compared to rods with open sections or slots. There was no noticeable deformation of the rods for all tests. The combined torque-rotation relationship for resorbable cement and PMMA cement is shown in FIGS. 16 and 18, respectively. FIG. 18 illustrates the averaged torque-rotation curve for all 6 specimens.

All PMMA specimens failed at less than 4.0 degrees of rotation. The failure mode of the PMMA was in sudden breaks of the cement, indicated by sudden drops in load. The initial change in load was considered to be the first case of failure. Resorbable specimens, however, failed in a different fashion; load continued to increase asymptotically toward a plateau, accompanied by continued rotation until failure was reached, often resulting in fracture of the bone. Resorbable specimens deformed at a significantly larger angle of rotation than PMMA specimens. In addition, torque at failure for the resorbable specimens was nearly twice that of the PMMA specimens. It is interesting to consider the rod-cement-bone mechanics at rotations greater than 4 degrees. The stiffness in this region has decreased, and the curves are indicative of plastic deformation. This deformation may be occurring in the cement as it is compressed by the rod.

Furthermore, there was more variability in the resorbable specimen's torque-rotation curves than the PMMA properties.

Figure 15:
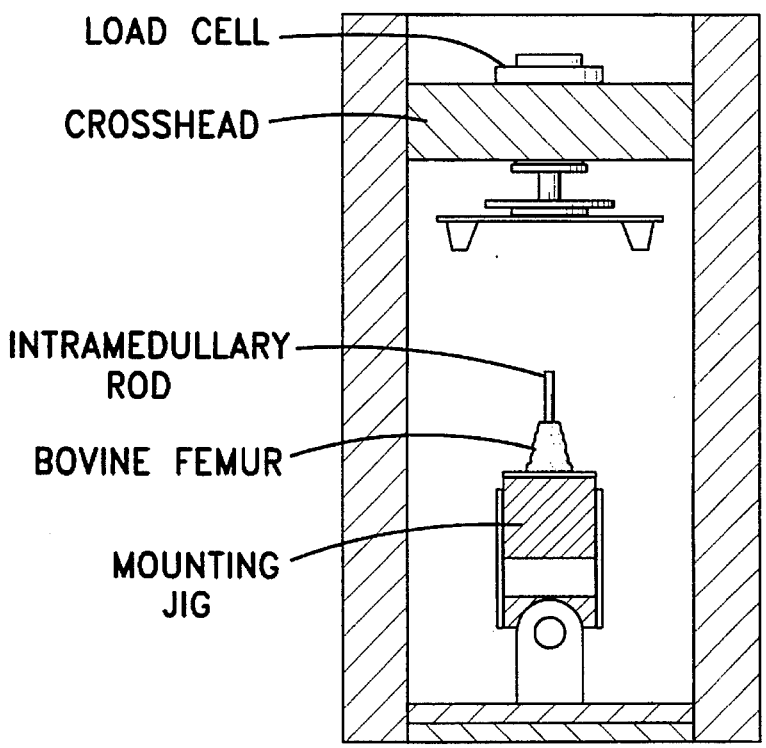
Figure 20:
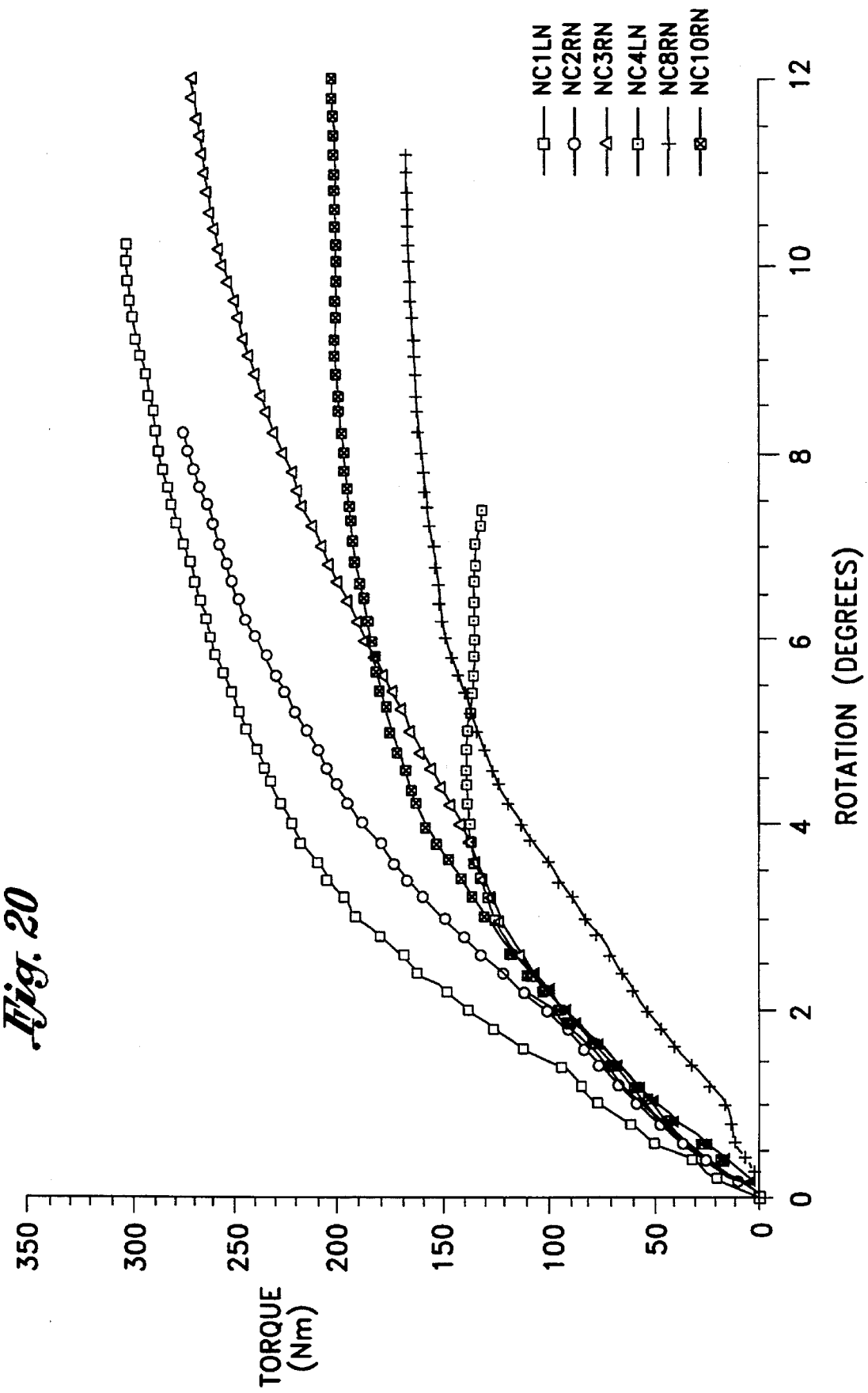
Figure 21:
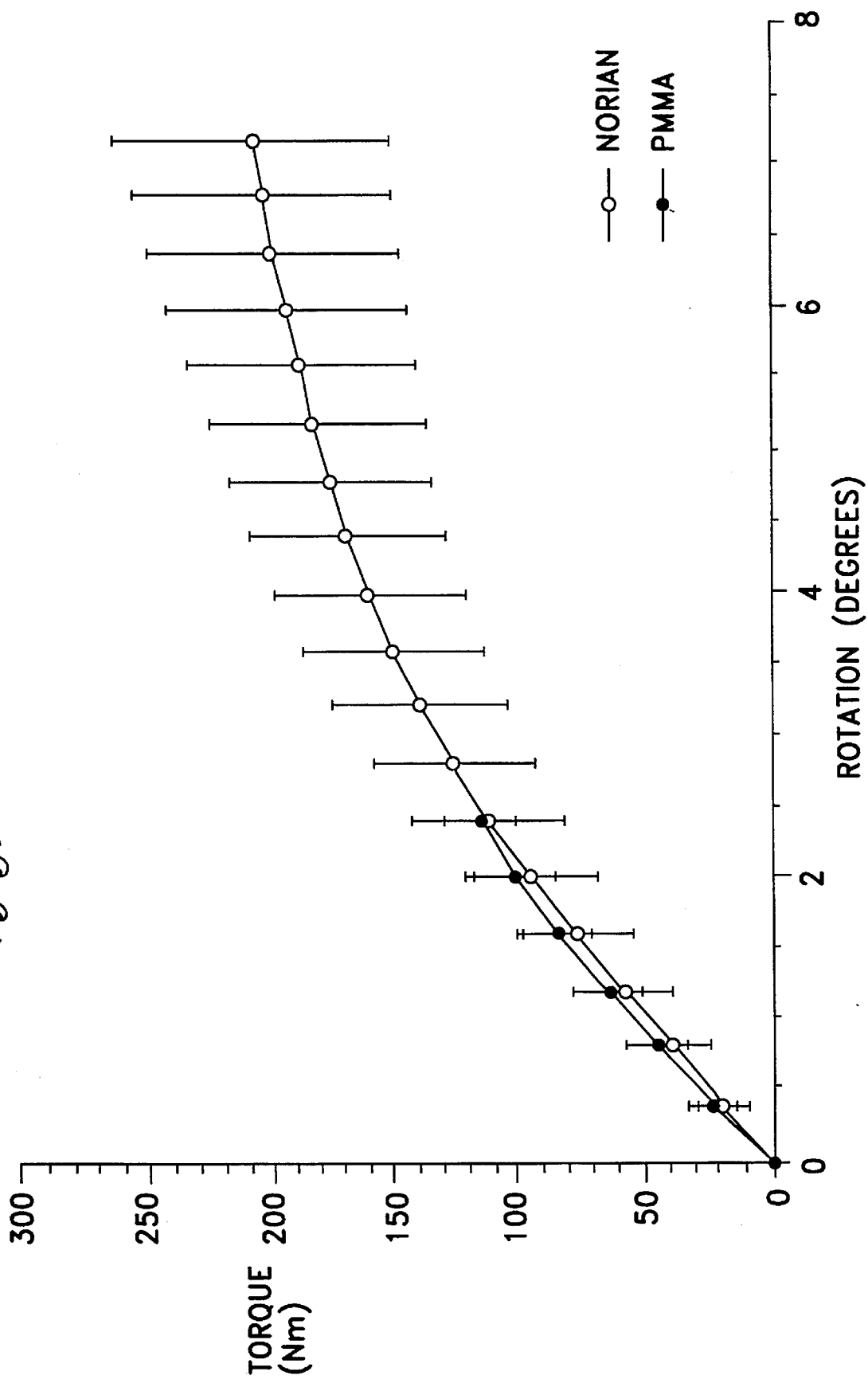

Summarizing the torsional properties, FIGS. 20 and 21 are of major significance to this study. Both torque at failure and rotation at failure were significantly larger for the resorbable specimens than for the PMMA specimens. These differences were statistically significant with $p=0.059$ for torque at failure and $p<0.001$ for rotation at failure. Finally, the torsional stiffness was calculated for both fixation systems. Stiffness was determined by performing a linear least squares curve fit within the range of 0.5 to 2.5 degrees of rotation, and are shown in FIG. 15. Stiffness values were nearly the same for both groups.

This lower range of rotation could be considered the working physiological range of the rod, and would indicate the performance of the resorbable cement to be comparable to that of the accepted PMMA cement. All properties are summarized in FIGS. 21 and 22.

The rods were extracted following testing and it was noted that the resorbable cement bonded to the rod, making rod extraction more difficult. In comparison, there was no bonding between the PMMA cement and the rods as evidenced by the ease of extraction. This bonding of the resorbable cement is believed to be a positive feature which would enhance the quality of fixation. We believe, however, that the bonding of the resorbable cements would not be so strong as to prevent rod extraction in clinical use, should that prove necessary.

D. Conclusions

Initial determination of stiffness and torque at failure demonstrate that the resorbable cements are strong enough, as presently configured, to withstand normal physiological loads with a reasonable safety factor.

EXPERIMENT II

In further support of the ability of the resorbable cements to operate effectively in distal fixation of an intramedullary device, we performed an experiment to determine the effects of injection of the resorbable cements. In the experiment a hollow rod was inserted into the intramedullary canal of bovine femurs as described above. However, instead of preapplication of the cement, cement was injected through the hollow rods. Similar curing procedures were followed.

A different cement formulation was utilized. The cement was obtained from Norian Corporation in Mountain View, Calif. and is sold as their Superbone® resorbable cement.

In subjecting the samples to similar tests as described above, we discovered that the samples injected Superbone® cement (Specimens Labelled NI) failed at a higher torque in torsion than did the previously evaluated formula M828 cement, and significantly higher than PMMA. Rotation at failure was similar for the Norian cements, while both failed at a larger angle than PMMA. The higher failure torque and similar rotational failure point are evident in the Torsional stiffness. The injected cement exhibited a larger stiffness ($64.5\pm17.4$ Nm/°) than did the M828 formulation ($44.7\pm4.1$ Nm/°). The final specimen (NI-4) exhibited a slightly different behavior than the other three injected specimens. This could have been a result of the delay between the first and second 50 g injection batch for this bone. This may be important in developing the delivery system in which there is no significant waiting period during the injection process.

Compressive stiffness for the injected cement was lower than the values for both PMMA and M828 in the previous study, with more variability than previously reported. This could be due to injection technique, or the difference in the cement formulation.

Figure 22:
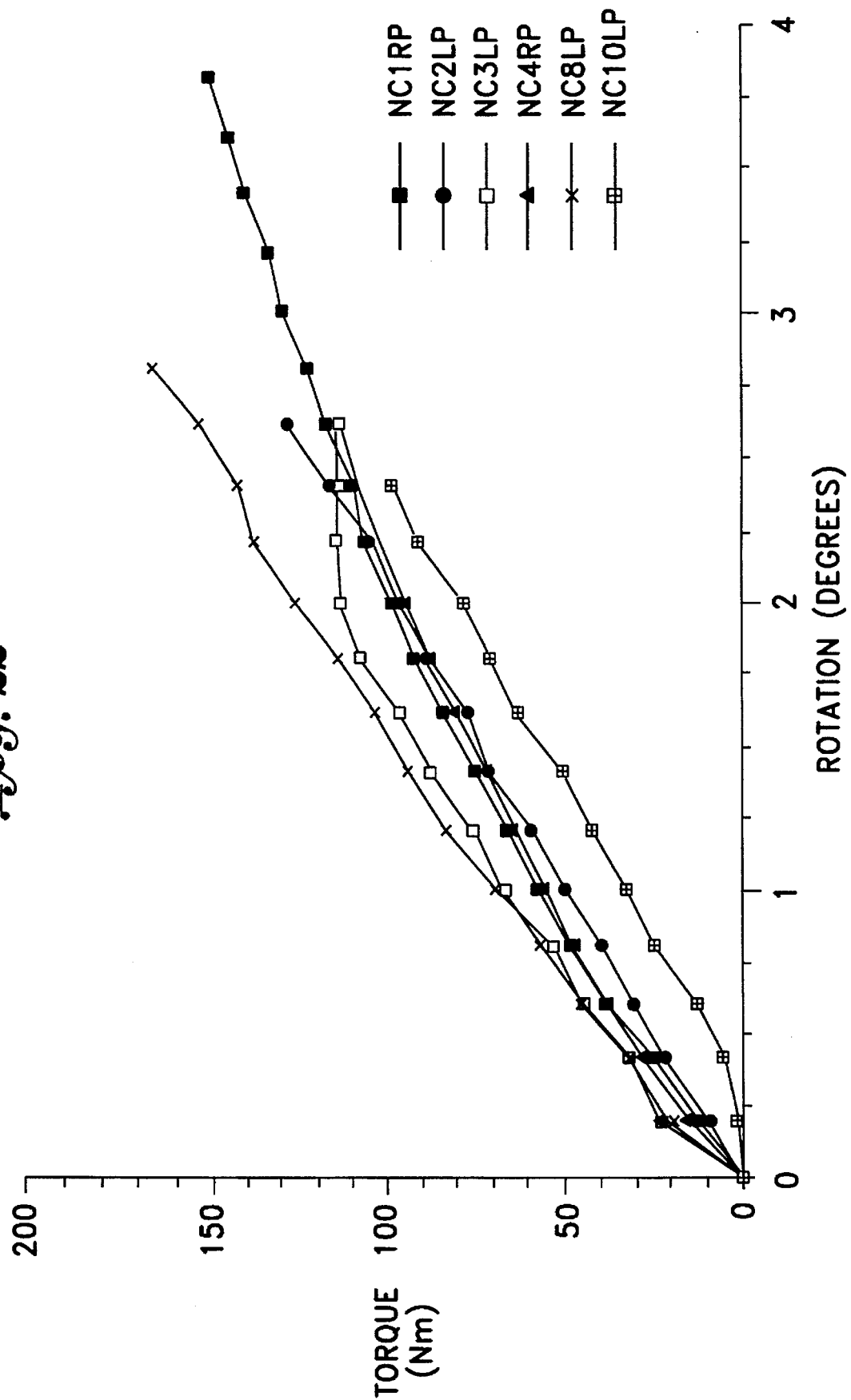

The data from the four tested bones is summarized below and is also shown in FIG. 22:

TABLE I

| Specimen | Norian Superbone - Injected Formulation | | | |
| --- | --- | --- | --- | --- |
| | Compressive Stiffness (N/mm) | Torsional Stiffness (NM/°) | Torque At Failure (NM) | Rotation at Failure (Degrees) |
| NI 1 | 4563.7 | 75.1 | 333.8 | 8.4 |
| NI 2 | 3695.8 | 78.0 | 304.0 | 7.6 |
| NI 3 | 2081.6 | 65.3 | 308.3 | 9.5 |
| NI 4 | 3195.3 | 39.7 | 224.1 | 13.6 |
| Average | 3384.1 | 64.5 | 292.6 | 9.8 |
| St Deviation | 1036.1 | 17.4 | 47.5 | 27. |

From this data, it will be seen that injection of the resorbable cement appears to enhance the strength of the fixation between the bone and the intramedullary device.

EXPERIMENT III

We also tested the mechanical properties of a polypropylene fumarate resorbable cement, available commercially from DynaGen, Cambridge, Mass. The cement was prepared pursuant to the manufacturer's instructions. Three sets of twelve bovine femurs were used in the experiments. The femurs were prepared as discussed in Experiments I and II.

In a first set of twelve femurs, cloverleaf rods were implanted and fixed with distal intramedullary screws. In a second set of twelve femurs, such rods were fixed in the femurs with Zimmer low viscosity cement (prepared in accordance with the manufacturer's instructions). And, a third set of twelve femurs were fixed with the DynaGen resorbable polypropylene fumarate cement. The cement was finger packed. Each of the femur/rod combinations were subjected to the same testing discussed above in connection with Experiments I and II.

Figure 28:
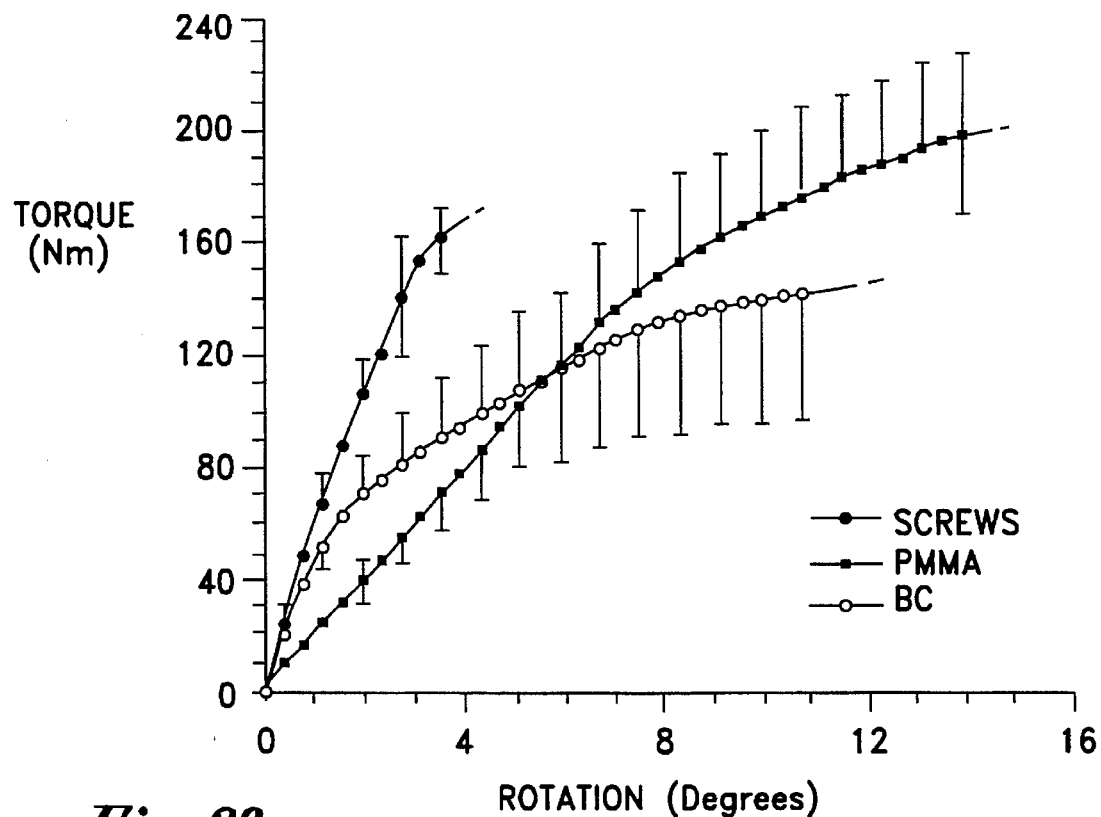

The results from these tests are shown in Table II and are graphed in FIG. 28.

TABLE II

Comparison of Interlocking, PMMA, and DynaGen Fixation

| Sample | Compressive Stiffness (N/mm) | Torsional Stiffness (NM/°) | Torque At Failure (NM) | Rotation at Failure (Degrees) |
|---|---|---|---|---|
| PPF | 4757 +/− 709 | 32 +/− 8 | 120 +/− 71 | 9.0 +/− 9.9 |
| PMMA | 4933 +/− 710 | 46 +/− 8 | 163 +/− 42 | 3.7 +/− 1.3 |
| IS | 2815 +/− 761 | 19 +/− 4 | 263 +/− 17 | 59.9 +/− 9.6 |

From this data, it will be seen that the DynaGen polypropylene fumarate (abbreviated PPF in Table II) resorbable cement is not quite as strong as the Norian materials. However, it provides a superior bond as compared to PMMA, particularly in rotation. The interlocking screw (abbreviated IS in Table II) method failed by a different mechanism, i.e., the screws and rods deformed without a loss of load thereby making it impossible to determine the point of initial deformation of the screws. However, with the method, there are the attendant severe problems of permanence and exposure to radiation.

EXPERIMENT IV

In connection with in vivo studies of the methods in accordance with the present invention, we plan to conduct a series of experiments described below.

A. SURGICAL PROTOCOL:

1. Overview

A total of 144 animals will be used in this study. The animals will be divided into 6 different time groups of 24 animals. Twelve will receive the experimental fixation and 12 will receive the standard cross screw transfixion. All animals will undergo a unilateral intramedullary nailing procedure. The grouping scheme can be outlined as follows (Table III, n=24 each group):

TABLE III

ANIMAL GROUP REVIEW

| Group | Phase | n | Study Time |
|---|---|---|---|
| 1 | 1 | 24 | 1 month |
| 2 | 2 | 24 | 2 months |
| 3 | 2 | 24 | 3 months |
| 4 | 2 | 24 | 6 months |
| 5 | 3 | 24 | 9 months |
| 6 | 3 | 24 | 12 months |

As shown, the study is divided into three phases. Phase 1, using animals in group 1, will serve as a feasibility study of intramedullary rod implantation, cement injection, and protocol refinement. Animals in phase 2 will be allowed to heal for 2, 3, and 6 months after surgery before sacrifice (the "short term healing group"). Phase 3 animals will go for longer time periods (9 and 12 months) and will provide data on long term effects of the cement fixation as well as allowing assessment of cement resorption (the "long term healing group").

2. Experimental Model

Figure 23A:
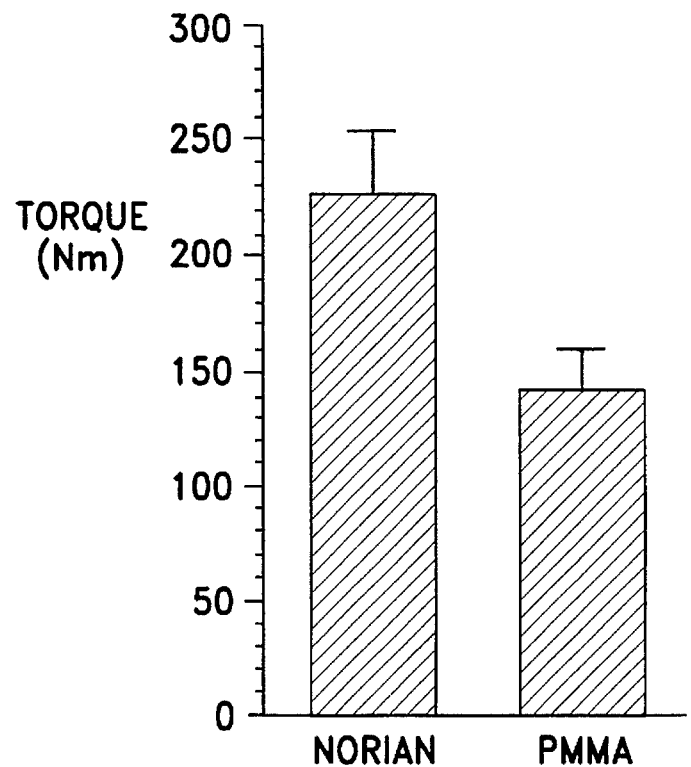
Figure 23B:
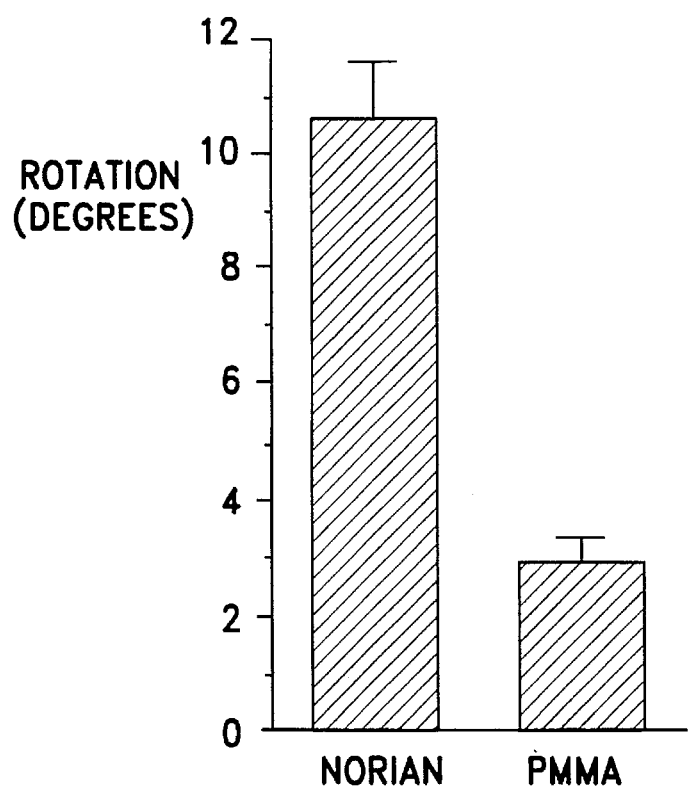
Figure 24A:
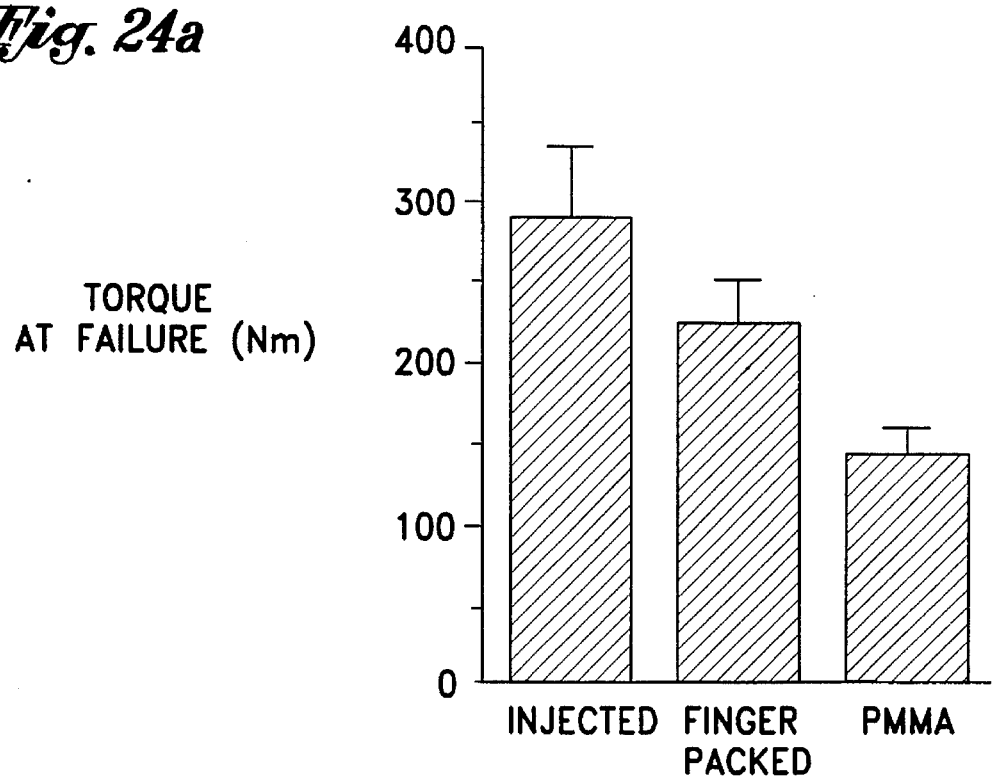
Figure 24B:
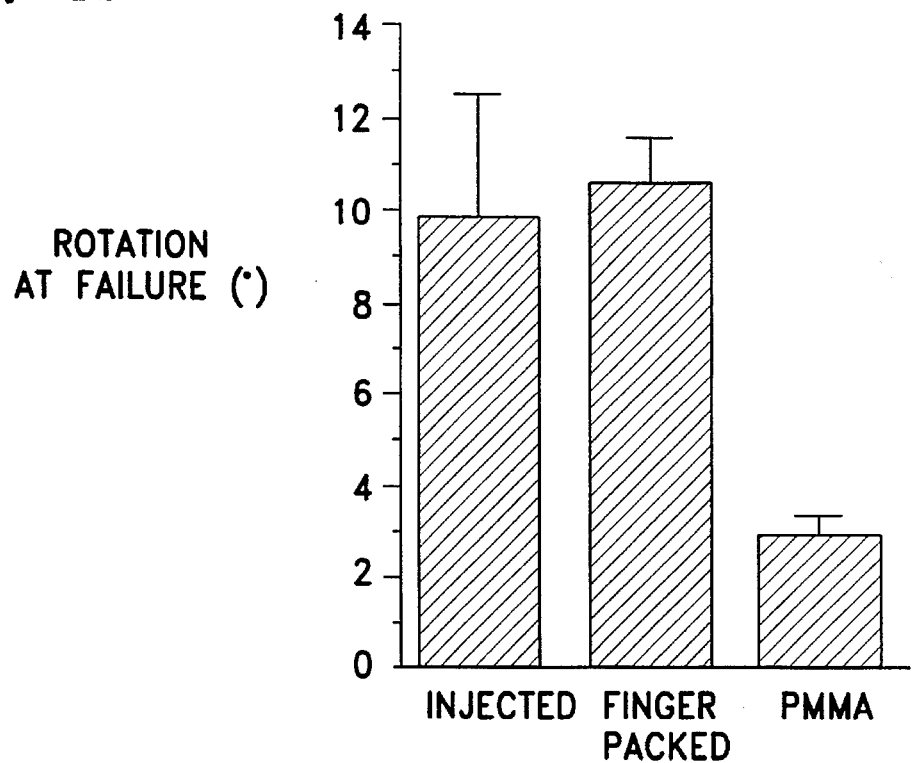
Figure 24C:
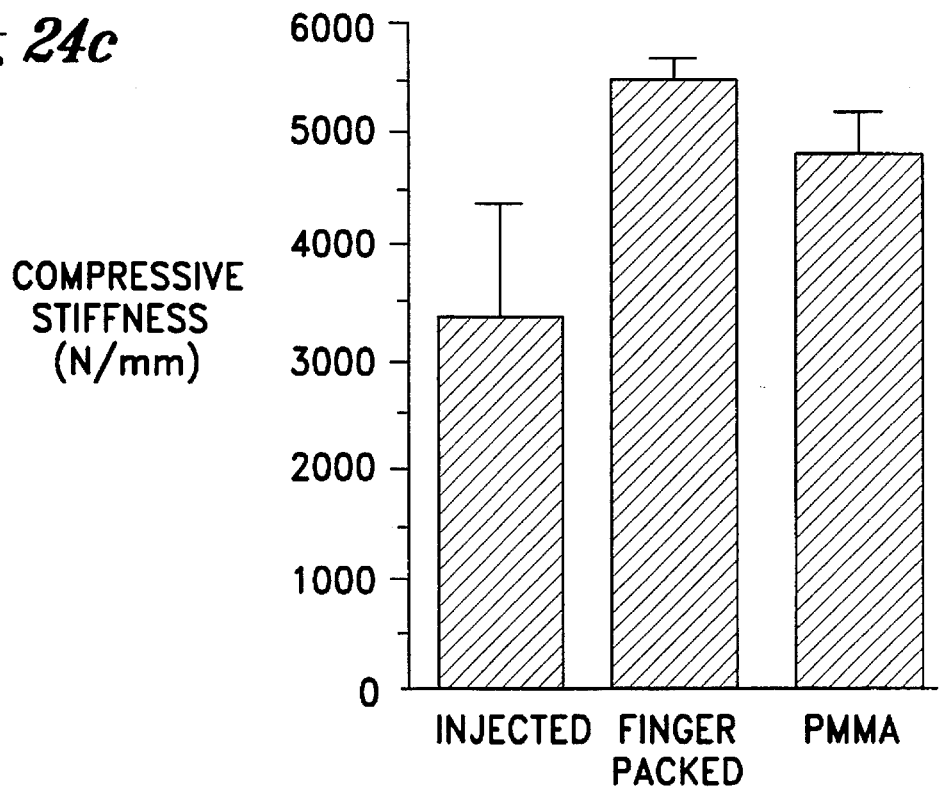
Figure 24D:
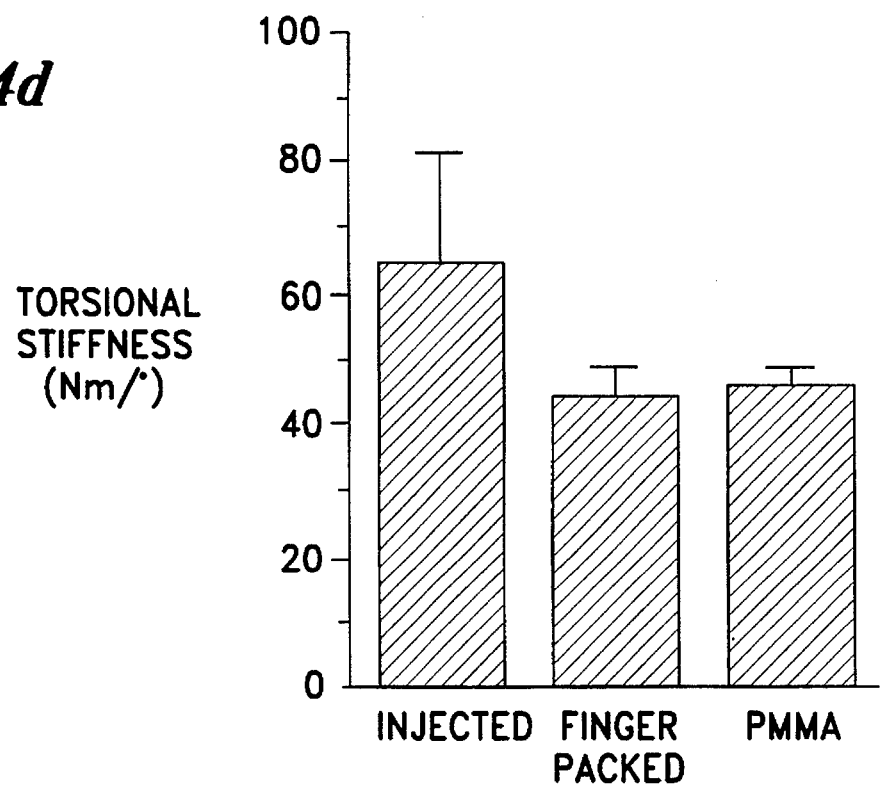

The experimental animal model for this project will be an animal femur selected from one of dog, sheep, baboon, or goat. A comminuted fracture 10 mm in length will be created in the proximal third of the left femur by removing this segment of bone. On half of the animals, an open intramedullary nailing technique will be performed using custom designed implants. The rod will be fixed with a single transfixion screw in the proximal femur, and with Norian Superbone® cement in the distal femur (FIG. 23). A cement delivery system will be employed allowing for cement injection down the length of the rod and into the distal femur.

The remaining 72 animals will undergo an open intramedullary nailing technique using a single transfixion screw proximally and two screws distally, with placement determined with an image intensifier targeting system. The wound will be closed and the femur X-rayed post-operatively (Anterior-posterior plane, and medial-lateral plane).

3. Healing Period

The animals will be allowed to heal for the time periods specified in Table III. X-rays will be taken to document progression of callus formation, bone union, and distal fixation with the cement. Pre-operative and post-operative X-rays are planned for all animals (Table IV). In addition, X-rays (both anterior-posterior plane, and medial-lateral plane) will be taken for each group according to the following Table:

TABLE IV

X-RAY SCHEDULE

| Group | # of X-rays | Week of X-Ray |
|---|---|---|
| 1 | 2 | 4 |
| 2 | 4 | 4 and 8 |
| 3 | 6 | 4, 8 and 12 |
| 4 | 8 | 4, 8, 12 and 24 |
| 5 | 10 | 4, 8, 12, 24 and 36 |
| 6 | 14 | 4, 8, 12, 24, 36, 48 and 52 |

4. Bone Growth

In order to assess the development of new bone at each time point, tetracycline labelling will be performed. Twelve animals from each group will receive tetracycline (declomycin 450 mg daily). Each animal will be given 1 dose of tetracycline per day for the 28 days prior to sacrifice. Assessment of the labelling will be discussed in the following experimental evaluation.

B. EXPERIMENTAL EVALUATION

In addition to quantitative assessment of all X-ray films for amount of callus and evidence of bone resorption around the fixation sites using an image analysis system, all specimens will be evaluated either histologically or biomechanically. Twelve animals from each group will be preassigned to either discipline as shown below (Diagram I):

DIAGRAM I

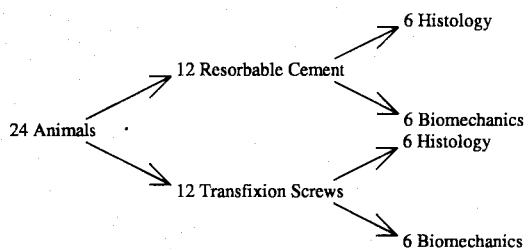

At sacrifice, both left and right femurs will be removed. The contralateral right femur will serve as control for each experimental (left) femur. At sacrifice, the femurs will be processed for either histological or biomechanical evaluation according to the corresponding protocol below.

The unilateral model will permit use of the control limb for time zero analysis. At sacrifice, the control (right) femur will be excised and the distal portion cut at the same level as the experimental femurs. The distal portion of the femur will be implanted with an intramedullary rod and fixed with either cement or transfixion screws. Torsional testing will be performed to determine the mechanical properties and will facilitate comparisons between time zero and longer term results.

1. Biomechanical Evaluation

At sacrifice, the left and right femurs from each animal will be removed, cleaned of all soft tissue, double wrapped in saline soaked gauze, and placed in plastic bags. The specimens will then be frozen for storage and transport prior to mechanical testing.

Each left femur will be tested in compression and torsion. The proximal fixation screw will be removed to free the proximal femur from the rod. A transverse cut will be made approximately 5 mm proximal to the level of the resorbable cement. Femurs employing transfixion screws will also be sectioned 20 mm above the level of the screws. This cut will not include the intramedullary rod, but rather leave it intact. The rod will be removed from the proximal femur and remain fixed in the distal femur. The distal portion will be subjected to compressive and torsional tests to evaluate the strength of the fracture callus. The testing protocol for the proximal and distal tests are described as follows.

a. Distal Femur Testing

The distal femur will be tested first in compression and then in torsion. The intramedullary rod will be cut to a minimum of 50 mm of rod extending from the femoral canal. The bone will be potted vertically in a custom designed chamber filled with Serroban low melting point metal (MP=158° C.). As the metal cools, it will conform to the shape of the condyles, holding the bone-rod complex securely in place. The chamber will be placed in an instron testing machine (FIGS. 13) and the rod will be loaded axially between 0 and 100N for 10 cycles at a rate of 10 mm/min using load control. The specimen will then be reoriented horizontally and fitted with a custom designed device permitting the application of a torsional force (FIG. 14). The specimen will be loaded from 0 Nm to 200 Nm, and then cycled between 100N and 200N for 10 cycles to precondition the system. The specimen will then be returned to the 100N load condition and torqued to failure (approx 100–300 Nm). The data will be collected using a computer-based data acquisition system.

b. Proximal Femur Testing

The proximal femur will be tested in torsion to determine the biomechanical strength of the fracture callus. The bone will be oriented vertically and potted at both the proximal and distal ends using a similar technique to that discussed for the distal femur, in this case making use of the low melt metal at both ends of the femur section. One potting chamber will then be fixed to the instron base and the opposing chamber attached to the torsion disc utilized for applying a force to the rod (FIG. 24). The specimen will be cycled between 100N and 200N for 10 cycles, and then torqued to failure. All data will also be collected using a computer-based data acquisition system.

c. Analysis

Data reduction and analysis will be performed using a custom software package specially written to evaluate the biomechanical data from the above tests. The compressive test will reveal the compressive stiffness of the rod-cement-bone complex and the rod-screw-bone complex (Units of N/mm). The torsional tests will be assessed to determine the torque at failure (Nm), the rod rotation at failure (°), the torsional stiffness (Nm/°), and the energy absorbed (Nm°). For phase 1 and 2 animals, statistical analysis of the results will be performed using a 2-way analysis of variance to determine the effect of healing time (1, 2, 3, 6 months) and fixation method (Norian Superbone® resorbable cement and transfixion screws). Phase 3 animals will be assessed using a 2-way analysis of variance (ANOVA) to determine the effect of healing after rod removal and fixation methodology. Post-hoc inter-group comparisons between time points and fixation methods will be performed. For all tests, the statistical level of significance will be $\alpha=0.05$.

C. BIOLOGY

Biological evaluation will be conducted on 12 animals from each group, 6 femurs in which Superbone is used for fixation and 6 in which transfixion screws are used. The evaluation will be performed at two sites. First, the healing callus will be quantified using a color based image analysis system. Second, the rate of bone ingrowth into the cement will be determined using quantitative histomorphometry. The quantity of cement injected into the distal femur will be measured on AP and lateral radiographs taken under controlled parameters (source distance, exposure time, voltage, etc.). These measures will allow the quantification of percent Superbone® resorption.

1. Histological Preparation and Analysis

Figure 25:
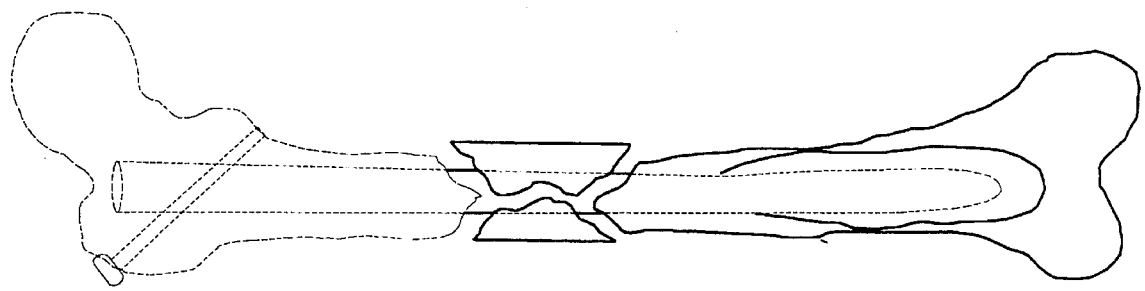
Figure 26:
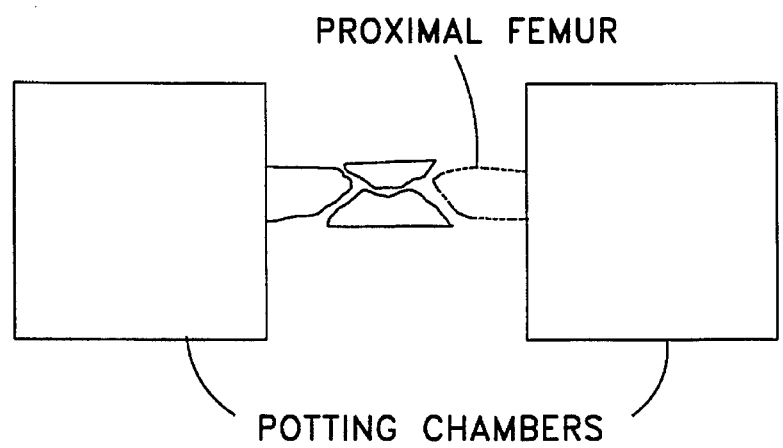
Figure 27:
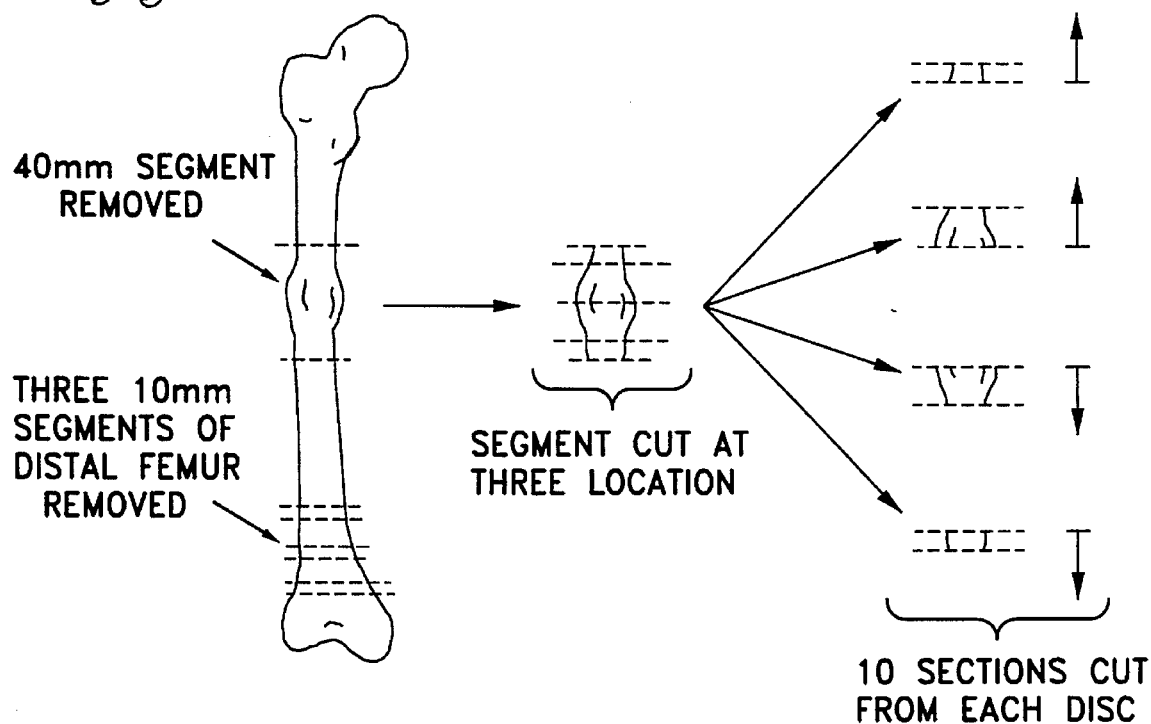

A 40 mm segment of bone will be removed from the proximal femur at the site of the fracture callus. This segment will consist of the healed 10 mm segment of bone as well as 10 mm of bone above and below the fracture site. Each of these three regions will be cut transversely. Histological sections will be prepared at each of the three regions, as shown in FIG. 25. The bone discs will be embedded in polymethylmethacrylate (PMMA). Sections 50 µm to 100 µm in thickness will be prepared and stained with McNeils basic fuchsin stain for light microscopy. Ultraviolet light excitation will be used for assessment of the tetracycline label. Ten slides from each section will be quantified for cortical, periosteal and endosteal new bone formation, porosity and old bone. Tetracycline labelled bone will be quantified under UV light. The quantity of bone and porosity will then be determined under transmission light. Subtracting new bone area from the total bone area will yield the area of old bone present. At the fracture site, it is expected that little old bone will be present and the total bone area will not be corrected in this manner.

Histology will be performed on the distal site of rod fixation. Representative sections will be cut from the proximal, middle, and distal portions of the area of cement fixation after rod extraction. Corresponding sections will be cut from the contralateral femurs as well as the femurs that have had screw fixation. Specimens will be embedded in PMMA prior to cutting. Approximately ten 50–100 µm sections will be cut on the Jung-Reichert microtome, polished, mounted, and stained with McNeils basic fuchsin. Analysis will be performed with a color-based image analysis system (American Innovision). Quantitative measures of cortical thickness and endosteal new bone formation, porosity, and old bone will be made. The amount of Superbone® present will also be quantified. In addition, areas of bone ingrowth into the cement will be quantified separately.

2. Statistics

Statistical analysis will be performed in similar fashion as the biomechanical statistics outlined above.

The foregoing description details specific methods and specific examples that can be employed to practice the present invention, and sets forth the best mode contemplated. However, it will be apparent to those of ordinary skill in the art that the disclosed embodiments may be modified without departing from the essence of the invention. For example, although the method of the present invention is specifically illustrated with respect to certain bone repair and augmentation techniques, it is equally suitable for utilization with any number of bones, intramedullary devices, prosthesis anchors, and the like, that can be readily adapted to meet specific requirements. Thus, however detailed the foregoing may appear in text, it should not be construed as limiting the overall scope hereof; rather, the ambit of the present invention is to be governed only by the lawful construction of the appended claims and any equivalents thereof.

We claim:

1. A method to repair a fractured bone that comprises the steps of:

reaming a canal in the bone to form a longitudinal channel extending from a first end to a second end of the bone, said channel having a proximal opening, a proximal portion and a distal end;

injecting an effective amount of a resorbable cement material into the distal end of the channel;

inserting into the channel an intramedullary rod, having a proximal end and a distal end, such that the distal end of the rod contacts said cement;

allowing said cement to cure thereby anchoring the rod to the bone, such that a bond strength between the rod and the bone is sufficient to withstand physiological loads during a healing period of the fracture until the bone can withstand normal physiological loads without augmentation; and leaving the intramedullary rod in place for sufficient time to allow the cement to undergo resorption, thereby allowing the rod to loosen so that stress shielding of the bone is reduced.

2. The method of claim 1, wherein the rod is hollow and has an opening in the distal end, and the inserting step precedes the injecting step, wherein the cement is injected through the rod so that the cement extrudes only from the opening in the distal end of the rod.

3. The method of claim 1 or claim 2, wherein the injecting step is accomplished by means of a device for introducing cement, wherein the device is used to inject cement directly into the canal or via the intramedullary rod that has a distal end opening that allows the cement to extrude therefrom.

4. The method of claim 2, wherein the rod further comprises interlocking aiming holes located opposite each other near the proximal end for securing the proximal end and the injecting step precludes discharge of cement through said holes by the use of a bypass nozzle that comprises:

an elongated shaft having a proximal end and a distal end and a lumen extending therebetween, said distal end sized to fit inside a proximal opening on the proximal end of the hollow rod and the shaft extends beyond the location of the aiming holes; and a connector on the proximal end constructed to receive and engage a feed container for introducing resorbable cement through the lumen.

5. The methods of claims 1 or 2, wherein said rod further comprises a plurality of grooves on the distal end to aid in providing greater contact between the cement and the rod and the insertion step places the grooves in contact with the cement.

6. The method of claim 1, wherein said resorbable cement material is a calcium derivative.

7. The method of claim 6, wherein said calcium derivative is generally composed of hydroxyapatite, orthophosphoric acid, calcium carbonate, and calcium hydroxide formed into a semi-liquid paste with an alkaline solution of sodium hydroxide and water.

8. The method of claim 1, wherein said resorbable cement material is a composition comprising polypropylene fumarate.

9. The method of claim 8, wherein the composition further comprises calcium salt filler, N-vinyl-2-pyrrolidone, and a peroxide or free radical initiator.

10. The method of claim 1, wherein the resorbable cement material comprises a mixture of calcium phosphates.

11. The method of claim 10, wherein the mixture comprises tetracalcium phosphate and dicalcium phosphate.

12. The method of claim 1, wherein said resorbable cement material further contains an active agent, selected from the group consisting of antibiotics, bone growth promoters, vasoactive agents, and other drugs.

13. The method of claim 1, further comprising, after the injecting and inserting steps, drilling a hole in the proximal end of the bone through the rod and inserting an interlocking device therethrough.

14. The method of claim 1, wherein said bone is selected from the group consisting of a femur, a tibia, a humerus, a radius, and an ulna.

15. A method to fix an orthopedic implant in a bone, comprising:

preparing the bone for implant insertion;

reaming a hole in the prepared bone, such that at least a portion of the cancellous tissue of the bone is exposed, said hole sized for the implant;

applying an effective amount of a resorbable cement, such that said cement provides contact surfaces between only a first portion of the implant that is in contact with the cancellous tissue of the bone; and allowing the cement to cure within the bone, such that fixation occurs between said first portion of the implant and a portion of the cancellous tissue of the bone through the cement and the contact surfaces, such that the fixation obtained is of sufficient strength to withstand physiological loads until fixation occurs by osteogenic growth between the bone and a second portion of the implant.

16. The method of claim 15, wherein the implant has a proximal end and a distal end, and a bore extending therebetween, and the inserting step precedes the applying step, wherein, in the applying step, the resorbable cement material is injected through the bore.

17. The method of claim 15, wherein the applying step comprises deploying the resorbable cement material onto the exposed cancellous tissue and onto the implant.

18. The method of claim 15, wherein said resorbable cement material is a calcium derivative.

19. The method of claim 18, wherein said calcium derivative is generally composed of hydroxyapatite, orthophosphoric acid, calcium carbonate, and calcium hydroxide formed into a paste with an alkaline solution of sodium hydroxide and water.

20. The method of claim 15, wherein said resorbable cement material is a composition comprising polypropylene fumarate.

21. The method of claim 20, wherein the composition further comprises calcium salt filler, N-vinyl-2-pyrrolidone, and a peroxide or free radical initiator.

22. The method of claim 15, wherein the resorbable cement material comprises a mixture of calcium phosphates.

23. The method of claim 22, wherein the mixture comprises tetracalcium phosphate and dicalcium phosphate.

24. The method of claim 15 or any one of claims 18 through 23, wherein said resorbable cement material further contains an active agent, selected from the group consisting of antibiotics, bone growth promoters, vasoactive agents, and other drugs.

25. The method of claim 15 or 16, wherein said implant has a substantially tubular structure.

26. The method of claim 25, wherein said implant is an intramedullary rod.

27. The method of claim 15, wherein said implant further comprises a plurality of grooves on the distal end to aid in providing greater contact between the cement and the implant and the fixation occurs between the implant and the bone through contact between the grooves and the cement.

28. The method of claim 15, wherein a cement introducer device is used in the applying step for injecting the resorbable cement.

29. The method of claim 26, wherein the rod has a proximal end and a distal end and a bore extending therebetween and the applying step further comprises injecting cement through said bore.

30. The method of claim 29, wherein the rod further comprises the interlocking aiming holes of claim 4 and the method further comprises the use of the bypass nozzle of claim 4 in the applying step.

31. A method to repair a comminuted fracture in a bone, comprising:
providing a bone having a comminuted fracture comprising one or more fragments each said fragment being separated by a space from a main portion of said bone;
applying a resorbable cement to said space; and
pushing each said fragment into a proper alignment with the main portion of said bone thereby substantially eliminating said space and forming a bond between said cement, said fragments, and said main portion of said bone.

32. The method of claim 31, further comprising the step of, after pushing step, holding said fragments and said main portion of said bone together.

33. The method of claim 32, wherein said holding step further comprises fitting plates around said fracture and screwing said plates to said bone.

34. The method of claim 32, wherein said holding step further comprises wrapping said fracture with circlage.

35. A method to inject cement into a cavity within a bone, comprising:
reaming a canal in the bone to form a longitudinal channel extending from a first end of the bone to a second end of the bone, said channel having a proximal opening, a proximal portion, and a distal end;
inserting a cement introducer device into the canal, wherein said introducer device comprises:
an elongate flexible shaft having a proximal end and a distal end and a lumen extending therebetween;
a connector on the proximal end for attaching a feed container containing a resorbable cement; and
a feed container attached to said connector containing resorbable cement, said feed container having means for pushing said cement from said container through said lumen and out the distal end of said shaft, and wherein said flexible shaft is inserted into said channel; and
injecting cement from said cement introducer device through said flexible shaft into said channel.

36. The method of claim 35, further comprising: inserting an intramedullary rod through said flexible shaft that has been inserted into said channel;
withdrawing said flexible shaft, thereby leaving said intramedullary rod in said channel; and allowing said cement to cure, thereby fixing said intramedullary rod to the bone.

\* \* \* \* \*